US012604902B2

(12) United States Patent
Hirsch et al.

(10) Patent No.: US 12,604,902 B2
(45) Date of Patent: Apr. 21, 2026

(54) BACTERIA FROM MEDICAGO ROOT NODULES AS PLANT PROBIOTIC BACTERIA FOR AGRICULTURE

(71) Applicants: THE REGENTS OF THE UNIVERSITY OF CALIFORNIA, Oakland, CA (US); B.G. Negev Technologies & Applications Ltd., at Ben-Gurion University, Beer-Sheva (IL)

(72) Inventors: Ann M. Hirsch, Los Angeles, CA (US); Pilar Martinez-Hidalgo, Los Angeles, CA (US); Drora Kaplan, Beer-Sheva (IL)

(73) Assignees: The Regents of the University of California, Oakland, CA (US); B.G. Negev Technologies & Applications. Ltd., at Ben-Gurion University, Beer-Sheva (IL)

( * ) Notice: Subject to any disclaimer, the term of this patent is extended or adjusted under 35 U.S.C. 154(b) by 1295 days.

(21) Appl. No.: 17/260,995

(22) PCT Filed: Jul. 17, 2019

(86) PCT No.: PCT/US2019/042244
§ 371 (c)(1),
(2) Date: Jan. 15, 2021

(87) PCT Pub. No.: WO2020/018694
PCT Pub. Date: Jan. 23, 2020

(65) Prior Publication Data
US 2021/0289793 A1 Sep. 23, 2021

Related U.S. Application Data

(60) Provisional application No. 62/700,003, filed on Jul. 18, 2018.

(51) Int. Cl.
| | |
|---|---|
| *A01N 63/20* | (2020.01) |
| *A01N 63/22* | (2020.01) |
| *A01N 63/25* | (2020.01) |
| *A01N 63/28* | (2020.01) |
| *C12N 1/205* | (2026.01) |
| *C12R 1/01* | (2006.01) |
| *C12R 1/07* | (2006.01) |
| *C12R 1/29* | (2006.01) |

(52) U.S. Cl.
CPC ............ *A01N 63/20* (2020.01); *A01N 63/22* (2020.01); *A01N 63/25* (2020.01); *A01N 63/28* (2020.01); *C12N 1/205* (2021.05); *C12R 2001/01* (2021.05); *C12R 2001/07* (2021.05); *C12R 2001/29* (2021.05)

(58) Field of Classification Search
None
See application file for complete search history.

(56) References Cited

U.S. PATENT DOCUMENTS

| | | |
|---|---|---|
| 6,194,193 B1 | 2/2001 | Drahos et al. |
| 2016/0143295 A1 | 5/2016 | Hirsch et al. |
| 2016/0183532 A1 | 6/2016 | Taghavi et al. |
| 2016/0312316 A1 | 10/2016 | Matheny et al. |
| 2017/0231230 A1 | 8/2017 | Dodda et al. |

FOREIGN PATENT DOCUMENTS

CN 102643766 8/2012

OTHER PUBLICATIONS

Abbasi et al., "Isolation of plant growth promoting rhizobacteria from wheat rhizosphere and their effect on improving growth, yield and nutrient uptake of plants" *Plant Biosystems—An International Journal Dealing with all Aspects of Plant Biology* 2011, 145(1), 159-168.

Bais et al., "The role of root exudates in rhizosphere interactions with plants and other organisms" *Annual Review of Plant Biology* 2006, 57, 233-266.

Benhizia et al. "Gamma proteobacteria can nodulate legumes of the genus *Hedysarum*. System." *Appl. Microbiol.* 2004, 27, 462-468.

Bérdy, János, "Bioactive microbial metabolites" *J. Antibiot.* 2005, 58(1), 1-26.

Chou et al., "*Labrys neptuniae* sp. nov., isolated from root nodules of the aquatic legume Neptunia oleracea." *Int. J. Syst. Evol. Microbiol.* 2007, 57, 577-581.

De Meyer et al., "Symbiotic Burkholderia species show diverse arrangements of nif/fix and nod genes, and lack typical high affinity cytochrome cbb3 oxidase genes." *Mol. Plant-Microbe Interact.* 2016, 29(8), 609-619.

Deng et al., "Diversity of endophytic bacteria within nodules of the Sphaerophysa salsula in different regions of Loess Plateau in China." *FEMS Microbiol. Ecol.* 2011, 76, 463-475.

Deng et al., "*Paracoccus sphaerophysae* sp. nov., a siderophore-producing, endophytic bacterium isolated from root nodules of Sphaerophysa salsula." *Int. J. Syst. Evol. Microbiol.* 2011, 61, 665-669.

Fox et al., "Enhanced nodulation and symbiotic effectiveness of Medicago truncatula when co-inoculated with Pseudomonas fluorescens WSM3457 and Ensifer (Sinorhizobium) medicae WSM419" *Plant Soil* 2011, 348, 245-254.

García-Fraile et al., "*Cohnella phaseoli* sp. nov., isolated from root nodules of Phaseolus coccineus in Spain, and emended description of the genus *Cohnella.*" *Int. J. Syst. Evol. Microbiol.* 2008, 58, 1855-1859.

Genilloud et al., "Current approaches to exploit actinomycetes as a source of novel natural products" *J Ind Microbiol Biotechnol* 2011, 38, 375-389.

(Continued)

*Primary Examiner* — Alton N Pryor
(74) *Attorney, Agent, or Firm* — Norton Rose Fulbright US LLP

(57) ABSTRACT

Methods and compositions for increasing one or more plant growth characteristics in a plant are disclosed. The compositions comprise one or more microbial isolates that promote plant growth. Methods include providing an effective amount of a composition comprising one or more microbial isolates that promote one or more plant growth characteristics.

19 Claims, 16 Drawing Sheets

(56) References Cited

OTHER PUBLICATIONS

Gyaneshwar et al., "Legumenodulating betaproteobacteria: diversity, host range, and future prospects." *Mol. Plant Microbe Interact.* 2011, 24, 1276-88.

Hirsch, Ann M. and Maria Valdes, "Micromonospora: An important microbe for biomedicine and potentially for biocontrol and biofuels" *Soil Biology & Biochemistry* 2010, 42, 536-542.

Hoque et al., "Genetic characterization of root-nodule bacteria associated with Acacia salicina and A. stenophylla (Mimosaceae) across southeastern Australia." *Int. J. Syst. Evol. Microbiol.* 2011, 61, 299-309.

Ibáñez et al., "Endophytic occupation of peanut root nodules by opportunistic Gammaproteobacteria. System." *Appl. Microbiol.* 2009, 32, 49-55.

Imran et al., "*Ochrobactrum ciceri* sp. nov., isolated from nodules of Cicer arietinum." *Int. J. Syst. Evol. Microbiol.* 2010, 60, 1548-1553.

International Search Report and Written Opinion issued in Corresponding PCT Application No. PCT/US2019/042244, dated Oct. 2, 2019.

Kalsi et al., "Phytases from *Enterobacter* and *Serratia* species with desirable characteristics for food and feed applications" *3 Biotech* 2016, 6(64), 1-13.

Kan et al., "Characterization of symbiotic and endophytic bacteria isolated from root nodules of herbaceous legumes grown in Qinghai-Tibet plateau and in other zones of China." *Arch. Microbiol.* 2007, 188, 103-115.

Lei et al., "Diverse bacteria isolated from root nodules of wild Vicia species grown in temperate region of China." *Arch. Microbiol.* 2008, 190, 657-671.

Li et al., "Biogeography of symbiotic and other endophytic bacteria isolated from medicinal *Glycyrrhiza* species in China." *FEMS Microbiol. Ecol.* 2011, 79, 46-68.

Martínez-Hidalgo et al., "Endophytic Micromonospora from Medicago sativa are apparently not able to fix atmospheric nitrogen." *Soil Biology and Biochemistry.* 2014, 74, pp. 201-203.

Martinez-Hidalgo et al., "Induced systemic resistance against Botrytis cinerea by Micromonospora strains isolated from root nodules" *Front. Microbiol.* 2015, 6(922), 11 pages.

Martinez-Hidalgo et al., "Micromonospora from nitrogen fixing nodules of alfalfa (*Medicago sativa* L.). A new promising Plant Probiotic Bacteria." *Scientific Reports* 4(6389), 11 pages.

Maymon et al., "Mining the phytomicrobiome to understand how bacterial coinoculations enhance plant growth." *Frontiers in Plant Science.* 2015, 6(784), pp. 1-14.

Murumkar et al., "Diversity for cell morphology, in-vitro phosphate solubilization and DNA profile of Bacillus megaterium isolates present in soils of Maharashtra." *World Applied Sciences Journal* 2012, 17(6), 776-785.

Pii et al., "Plant-microorganism-soil interactions influence the Fe availability in the rhizosphere of cucumber plants" *Plant Physiology and Biochemistry* 2015, 87, 45-52.

Spence et al., "Probiotics for Plants: Importance of Rhizobacteria on Aboveground Fitness in Plants" *Bacteria in Agrobiology: Plant Probiotics* 2012, 1-14.

Stajković et al., "Isolation and characterization of endophytic non-rhizobial bacteria from root nodules of alfalfa (*Medicago sativa* L.)." *Botanica serbica* 2009, 33, 107-114.

Sturz et al., "Biodiversity of endophytic bacteria which colonize red clover nodules, roots, stems and foliage and their influence on host growth." *Biology and Fertility of Soils* 1997, 25, 13-19.

Trujillo et al., "*Micromonospora lupini* sp. nov. and *Micromonospora saelicesensis* sp. nov., isolated from root nodules of Lupinus angustifolius." *International Journal of Systematic and Evolutionary Microbiology* 2007, 57, 2799-2804.

Trujillo et al., "The genus *Micromonospora* is widespread in legume root nodules: the example of Lupinus angustifolius." *ISME J* 2010, 4, 1265-1281.

Valdés et al., "Non-Frankia Actinomycetes isolated from surface sterilized roots of Casuarina equisetifolia fix nitrogen." *Applied and Environmental Microbiology* 2005, 71, 460-466.

Valverde et al., "*Herbaspirillum lusitanum* sp. nov., a novel nitrogen-fixing bacterium associated with root nodules of Phaseolus vulgaris." *Int. J. Syst. Evol. Microbiol.* 2003, 53, 1979-1983.

Velazquez et al. "Nodular Endophytes: An Untapped Diversity." *Beneficial Plant-microbial Interactions: Ecology and Applications*, edited by M. Belén Rodelas González and Jesús González-López, CRC Press, 2013, 214-235.

Velázquez et al., "Proteobacteria Forming Nitrogen Fixing Symbiosis with Higher Plants." *Proteobacteria: Phylogeny, Metabolic Diversity and Ecological Effects*, edited by M.L. Sezenna, 1st ed., New York, U.S.A., Nova Science Publishers Inc., 2011, pp. 37-56.

Vessey, Kevin J., "Plant growth promoting rhizobacteria as biofertilizers" *Plant and Soil* 2003, 255, 571-586.

Zakhia et al., "Diverse bacteria associated with root nodules of spontaneous legumes in Tunisia and first report for nifH like gene within the genera Microbacterium and Starkeya." *Microb. Ecol.* 2006, 51, 375-393.

Ali et al., "Isolation and molecular characterization of polyvinyl chloride (PVC) plastic degrading fungal isolates", J Basic Microbial., 54(1):18-27, 2014.

Angus et al. "Plant-Associated Symbiotic Burkholderia Species Lack Hallmark Strategies Required in Mammalian Pathegenesis." PLOS One, vol. 9: 1-12, 2014.

Bharti et al., "Plant growth promoting rhizobacteria Dietzia natronolimnaea modulates the expression of stress responsive genes providing protection of wheat from salinity stress" *Scientific Reports* 2016, 6:34768, 16 pages.

Boyle et al., "Solubilization and mineralization of lignin by white rot fungi", Appl Environ Microbial., 58(10):3217-3224, 1992.

Buck et al., "Perfluoroalkyl and polyfluoroalkyl substances in the environment: terminology, classification, and origins", Integr Environ Assess Manag., 7(4):513-541, 2011.

Butt et al., "Biotransformatoin pathways of fluorotelomer-based polyfluoroalkyl substances: a review", Environ Toxicol Chem., 33(2):243-267, 2014.

Ceci et al., "Biotransformation of 13-hexachlorocyclohexane by the saprotrophic soil fungus Penicillium griseofulvum", Chemosphere, 137:101-107, 2015.

Chinnaswamy et al., "A nodule endophytic Bacillus megaterium strain isolated from Medicago polymorpha enhances growth, promotes nodulation by Ensifer medicae and alleviates salt stress in alfalfa plants" *Annals of Applied Biology* 2018, 172, 295-308.

Database JGI Genome Portal [Online]; Jun. 2018 (Jun. 2018), "Dietzia cinnamea 55" Database accession No. 1144511.

Gharihzahedi et al., "Potential applications and emerging trends of species of the genus *Dietzia*: a review" *Ann Microbiol*, 2014, 64:421-429.

Harms et al., "Untapped potential: Exploiting fungi in bioremediation of hazardous chemicals", *Nat Rev Microbial*, 9(3):177-192, 2011.

Hayat et al., "Soil beneficial bacteria and their role in plant growth promotion: a review" *Ann Microbiol* 2010, 60:579-598.

International Search Report and Written Opinion for PCT/US2014/041779, mailed Dec. 29, 2014.

Kaplan et al., "A Survey of the Microbial Community in the Rhizosphere of Two Dominant Shrubs of the Negev Desert Highlands, Zygophyllum Dumosum (Zygophyllaceae) and Atriplex Halimus (Amaranthaceae), Using Cultivation-Dependent and Cultivation-Independent Methods," *Am. J. Botany*, 100(9): 1713-1725, 2013.

Kim et al., "Biodefluorination and biotransformation of fluorotelomer alcohols by two alkane-degrading Pseudomonas strains." *Biotechnol Bioeng*; 109(12):3041-3048, 2012.

Liu et al., "6-2 Fluorotelomer alcohol aerobic biodegradation in soil and mixed bacterial culture", *Chemosphere*, 78(4):437-444, 2010.

Merino et al., "Degradation and Removal Methods for Perfluoroalkyl and Polyfluoroalkyl Substances in Water", *Environmental Engineering Science*, 33(9):615-649, 2016.

Ning et al., "Involvement of Cytochrome P450 in Pentachlorophenol Transformation in a White Rot Fungus Phanerochaete chrysoporium", *PLoS One*, 7(9):e45887, 2012.

(56) References Cited

OTHER PUBLICATIONS

Partial Supplementary European Search Report issued in Corresponding European Application No. 19837725.1, dated Mar. 18, 2022.

Rathnayake, "Development of Whole-Cell Microbial Biosensors to Assess the Heavy Metal Bioavailability in the Soil Environment." *University of South Australia*, pp. 1-218, 2010.

Roberts et al., "Biocontrol agents applied individually and in combination for suppression of soilborne diseases of cucumber", *Crop Protection* 24(2) :141-155, 2005.

Ruan et al., "Aerobic soil biotransformation of 6:2 fluorotelomer iodide", *Environ Sci Technol*, 47(20):11504-11511, 2013.

Schwartz et al. "Bacillus simplex-A Little Know PGPB with Anti-Fungal Activity-Alters Pea Legume Root Architecture and Nodule Morphology When Coinoculated with *Rhizobium leguminosarum* bv. Viciae." *Agronomy*, vol. 3: 595-620, 2013.

Subramanian et al., "Role of P450 Monooxygenases in the Degradation of the Endocrine-Disrupting Chemical Nonylphenol by the White Rot Fungus Pharnerochaete chrysosporium", *Environ. Microbial.*, 75(17) :5570-5580, 2009.

Sun et al., "Bacterial community compositions in sediment polluted by perfluoroalkyl acids (PFAAs) using Illumina high-throughput sequencing", *Environ Sci Pollut Res Int.*, 23(11) :10556-10565, 2016.

Tak et al., "Advances in the Application of Plant Growth-Promoting Rhizobacteria in Phytoremediation of Heavy Metals", *Reviews of Environmental Contamination and Toxicology*, 223:33-52, 2012.

Tseng et al., "Biotransformation of 6:2 fluorotelomer alcohol (6:2 FTOH) by a wood-rotting fungus", *Environ Sci Technol.*, 48(7):4012-4020, 2014.

Von Der Weid et al., "Identification and biodegradation potential of a novel strain of Dietzia cinnamea isolated from a petroleum-contaminated tropical soil" *Systematic and Applied Microbiology* 2007, 30, 331-339.

Wang et al., "8-2 fluorotelomer alcohol aerobic soil biodegradation: pathways, metabolites, and metabolite yields", *Chemosphere*, 75(8):1089-1096, 2009.

Zhang et al., "Impact of 6:2 fluorotelomer alcohol aerobic biotransformation on a sediment microbial community", *Sci Total Environ.*, 575:1361-1368, 2017.

Zhao et al., "6:2 fluorotelomer alcohol biotransformation in an aerobic river sediment system", *Chemosphere*, 90(2):203-209, 2013.

| Strains | CAS | P. solubilization | N free medium | CMC | C source CMC | C source Pectin | C source Xylan | Casein | pH 4.5 | pH 5.5 | pH 6 | pH 8 | pH 9 | NaCl1% | NaCl3% | NaCl5% |
|---|---|---|---|---|---|---|---|---|---|---|---|---|---|---|---|---|
| 2u118 | + | ~ | + | ~ | + | ~ | ~ | ~ | ~ | + | + | + | + | ~ | ~ | ~ |
| USAFOC10 | ~ | ~ | + | +++ | + | ~ | + | ~ | + | + | + | + | + | + | + | + |
| 1u117 | ~ | ~ | + | + | + | ~ | ~ | + | + | + | + | + | + | + | + | + |
| 2u16 | ~ | ~ | + | ~ | + | ~ | ~ | ~ | ~ | + | ~ | + | + | + | ~ | ~ |
| 2u27 | ~ | ~ | + | ~ | + | ~ | ~ | ~ | ~ | + | ~ | + | + | + | ~ | ~ |
| 1u19 | ~ | ~ | + | ~ | + | ~ | ~ | ~ | ~ | + | + | + | + | + | ~ | + |
| 4650D | + | ~ | + | ~ | + | ~ | + | ~ | ~ | + | + | + | + | ~ | ~ | ~ |
| 4677A | ~ | ~ | + | ~ | + | + | ~ | ~ | ~ | + | + | + | ~ | ~ | ~ | ~ |
| 1u115 | ~ | ~ | + | ~ | + | ~ | na | ~ | ~ | + | + | + | + | na | na | na |
| 2u15 | + | ~ | + | ++ | + | ~ | ~ | ~ | ~ | + | + | + | + | + | ~ | ~ |
| 2u111 | ~ | ~ | + | ~ | + | + | ~ | ~ | ~ | + | + | + | + | + | + | + |
| 1u113 | ~ | ~ | + | ~ | + | ~ | ~ | ~ | ~ | + | + | + | + | ~ | ~ | ~ |
| 1u24b | ~ | ~ | + | ~ | + | + | ?+ | ~ | + | + | + | + | + | + | ?+ | ?+ |
| 4650F | ~ | ~ | + | ~ | + | ~ | ~ | na | ~ | + | + | + | + | ~ | ~ | ~ |
| USAF16 | ~ | ~ | + | ~ | ?+ | ~ | ~ | ~ | ~ | ~ | ~ | + | ?+ | + | ~ | ~ |
| USAFOC8 | ~ | + | + | + | + | ~ | ~ | ~ | ~ | + | + | + | + | + | + | + |
| 1u10 | ~ | ~ | + | ~ | + | + | ~ | na | ?+ | + | + | + | + | ~ | ~ | ~ |
| USAFOna 16 | + | ~ | + | + | + | + | na | na | + | + | + | + | + | na | na | na |
| 2u210 | ~ | + | + | ++ | + | ~ | + | ~ | + | + | + | + | + | + | + | + |
| USAFOC17 | ~ | ~ | + | + | + | ~ | ++ | + | ~ | + | + | + | + | + | + | + |
| 2u13 | ~ | ~ | ~ | ~ | + | ~ | + | ~ | ~ | + | + | + | + | + | + | + |
| 2u114 | ~ | ~ | ~ | ~ | + | ~ | ~ | ?+ | ~ | + | + | + | + | + | + | + |
| USAF6 | + | ~ | + | ~ | + | + | na | na | ~ | + | + | + | + | na | na | na |
| USAFON2 | ~ | ~ | + | +++ | + | + | + | ++ | + | + | + | + | + | + | + | + |
| 2u110 | ~ | ~ | + | ~ | + | + | ~ | na | ~ | + | + | + | + | ?+ | ~ | ~ |
| 2u112 | ~ | + | + | ~ | + | + | ?~ | ~ | + | + | + | + | + | + | + | + |
| 1u118 | ~ | + | + | ~ | + | + | ?~ | na | ~ | + | + | + | + | ~ | ~ | ~ |
| 1u111 | ~ | ~ | + | ~ | + | + | ?~ | na | ~ | + | + | + | ~ | ~ | ~ | ~ |
| utrum1 | ~ | ~ | ~ | ~ | + | ~ | ?~ | + | ~ | ~ | ~ | + | + | + | + | + |
| 2u18 | + | ~ | + | ~ | + | + | ?~ | ~ | ~ | + | + | + | + | + | ~ | ~ |
| 1u116 | + | ~ | + | ~ | + | ~ | ?~ | na | ~ | + | + | + | + | ~ | ~ | ~ |
| USAFON3 | ~ | ~ | ~ | ~ | + | ~ | ?~ | ~ | ~ | ~ | ~ | + | + | ~ | ~ | ~ |
| USAFON1 | ~ | + | + | ~ | + | + | + | ~ | ~ | + | + | + | + | + | + | + |
| USAFOna6 | ~ | + | + | ++ | + | + | ~ | + | ~ | + | + | + | + | + | + | ~ |
| USAF17 | ~ | + | + | ~ | + | + | ~ | ~ | ~ | + | + | + | + | + | + | + |
| 1u112a | ~ | ~ | ~ | + | ~ | + | ~ | na | ~ | + | + | + | + | ~ | ~ | ~ |

FIG. 5A

| Strains | CAS | P solubilization | N free medium | CMC | C source CMC | C source Pectin | C source Xylan | Casein | pH 4.5 | pH 5.5 | pH 6 | pH 8 | pH 9 | NaCl1% | NaCl3% | NaCl5% |
|---|---|---|---|---|---|---|---|---|---|---|---|---|---|---|---|---|
| USAF29PDA | - | - | + | - | + | + | + | - | + | + | + | + | + | + | + | - |
| 2u24 | - | + | + | - | + | + | - | - | + | + | + | + | + | + | ++ | + |
| USAF1 | - | - | - | - | - | - | na | na | - | - | - | + | - | na | na | na |
| 1u114 | + | + | + | - | + | - | ?- | na | - | + | + | + | + | - | - | - |
| 2u17 | + | + | + | - | + | - | ?- | na | - | + | + | + | + | - | - | - |
| USAF6 | - | + | + | - | + | - |  | na | - | + | + | + | + | na | na | na |
| USAFOra4 | + | - | + | - | + | - | + | + | - | + | + | + | + | + | + | + |
| UTRUM1 | + | - | + | - | + | - | + | + | - | + | + | + | + | + | + | + |
| USAFOC20 | - | + | + | - | + | - | + | + | + | + | + | + | + | + | + | - |
| 4650D | + | + | + | - | + | - | na | na | - | + | + | + | + | na | na | na |
| USAFOC6 | - | + | + | - | + | - | ?- | + | + | + | + | + | + | + | + | + |
| PSB72 | - | - | + | - | + | - | - | + | - | + | + | + | + | + | + | + |
| PSB33 | - | + | + | + | + | - | + | - | - | + | + | + | + | + | + | + |
| PSB32 | - | - | - | - | + | - | - | - | + | - | + | + | + | + | + | - |
| 2S(Ca)4 | - | - | - | + | + | - | + | na | - | + | + | + | + | + | + | + |
| PSB36 | - | - | + | + | + | - | + | + | - | + | + | + | + | + | + | + |
| 1SB12 | - | - | - | - | - | - | + | + | - | + | - | + | + | + | + | + |
| PSB43' | - | + | - | - | + | - | na | na | - | + | + | + | + | na | + | + |
| PSB43 | - | + | + | + | + | - | + | + | + | + | + | + | + | + | + | + |
| 1SA(Ca)5 | - | + | + | + | - | - | + | + | + | + | + | + | + | + | + | + |
| 1SD10 | - | - | - | na | - | - | + | + | + | + | na | + | + | + | + | + |
| 2S(Ca)9 | - | + | - | - | - | - | na | + | - | - | + | + | + | + | - | - |
| PSCa3 | - | - | - | + | - | - | + | - | - | - | + | + | + | + | + | + |
| PSCa18 | - | - | + | + | + | - | + | - | - | + | + | + | - | + | + | + |
| PSCa25 | - | - | + | + | - | - | + | - | - | + | + | + | + | + | + | - |
| 2S4 | - | + | - | - | + | - | - | - | - | + | + | + | + | + | + | - |
| 15Sd13 | - | + | - | + | - | - | - | - | - | + | + | + | + | + | + | - |
| PSB34 | - | + | + | - | + | - | + | - | - | + | + | + | + | + | + | + |
| 1SB7 | - | - | + | - | - | - | - | - | - | + | + | + | + | + | + | + |
| PSB74 | + | + | - | + | + | + | - | - | - | + | + | + | + | + | + | + |
| PSCa21 | - | - | + | - | + | - | + | - | + | + | + | + | + | + | + | + |
| PSB30 | - | - | + | + | + | - | + | + | - | + | + | + | + | + | + | + |
| PSCA15 | + | - | - | + | - | - | - | - | - | + | + | + | - | - | - | - |
| PSCA26 | - | - | + | + | + | - | + | + | - | + | + | + | + | + | + | - |
| 1SD9 | - | - | - | + | + | - | + | - | - | + | + | + | + | + | + | + |
| 1SB6 | - | - | + | - | + | - | - | - | - | + | + | + | + | + | + | + |

FIG. 5B

BACTERIA FROM MEDICAGO ROOT NODULES AS PLANT PROBIOTIC BACTERIA FOR AGRICULTURE

CROSS-REFERENCE TO RELATED APPLICATIONS

This application is a national phase application under 35 U.S.C. § 371 of International Application No. PCT/US2019/042244, filed Jul. 17, 2019, which claims the benefit of priority of U.S. Provisional Patent Application No. 62/700,003 filed Jul. 18, 2018, which is hereby incorporated by reference in its entirety.

STATEMENT OF GOVERNMENT SUPPORT

This invention was made with government support under 1201735, awarded by the National Science Foundation. The government has certain rights in the invention.

BACKGROUND OF THE INVENTION

Modern agricultural practices rely extensively on use of chemicals—including synthetic fertilizers, pesticides, and herbicides—as well as techniques such as the genetic modification of plant germplasm, to produce characteristically high crop yields. Concerns about the environmental and health risks involved in heavy use of synthetic chemicals have forced a reexamination of the costs and benefits of such practices (Olivares et al., 2013; Pii et al., 2015). There is an environmentally sound and cost-efficient alternative, involving the application of beneficial bacteria known as plant probiotics (Spence et al., 2012; Martínez-Hidalgo et al., 2014). These bacteria are also known as plant-growth promoting microbes (PGPM), which may refer to a wide variety of soil microbes that colonize the rhizosphere and directly or indirectly stimulate growth in their host (Abbasi et al., 2011; Vessey, 2003). They do so by a number of mechanisms including fixing nitrogen, secreting plant hormones or antibiotics, lowering ethylene levels in plants, freeing phosphate and micronutrients from insoluble sources (Schwartz et al., 2011; Spence et al., 2012), and stimulation of disease-resistance mechanisms (Martínez-Hidalgo et al. 2015). In addition, some PGPM can directly fight off phytopathogens by the production and secretion of secondary metabolites.

PGPM form intimate relationships with their host plants in numerous, complex ways. Plants recruit PGPM by exuding compounds that alter the physical and chemical composition of the rhizosphere soil (Bais et al., 2006; Pii et al., 2015). PGPM respond to these cues and either intensively colonize the root surface or make their way inside the apoplastic spaces of the host plant to live as endophytes (Vessey, 2003). The classic example of this sort of endophytic relationship is the legume-rhizobial symbiosis, in which certain Gram-negative bacteria induce the formation of root nodules in their plant host, where they provide fixed nitrogen in exchange for carbon and the protective niche of the nodule interior. However, many other bacteria have been found in nodules that confer benefits to the plant in spite of not being able to reinfect the plant and form nodules by themselves (Velazquez et al., 2013). Many of these bacteria are PGPM that increase the efficiency of the legume-*Rhizobium* symbiosis. Nodule-forming, nitrogen-fixing *rhizobia* have been found to associate with helper bacteria, which can increase the number of nodules and/or shoot biomass, and in some cases enhance biological nitrogen fixation (Vessey 2003, Martinez-Hidalgo et al. 2014, Fox et al. 2011).

Studies of PGPM have generally focused on Gram-negative bacteria because they are readily isolated from plant tissues, generally more easy to handle, and amenable to genetic approaches. Recently though, the impact of Gram-positive bacteria, such as Firmicutes and Actinobacteria, in plants has been shown to be more important than was initially thought, with diverse activities such as biofertilization (through nutrient solubilization and phytohormone production), biocontrol (through antibiosis, mycoparasitism, induced systemic resistance), and bioremediation of heavy metals (Francis et al., 2010; Velazquez et al., 2013). An important order of actinobacteria is the Actinomycetales. The role of actinomycetes as potent degraders of complex biopolymers has long been acknowledged in compost heaps, decaying plant material, and manure piles. These bacteria can degrade tough structural polysaccharides such as cellulose, chitin, and lignin. Some actinomycetes can even degrade natural rubber (Jendrossek et al., 1997; Rose and Steinbüchel, 2005). In addition to synthesizing hydrolytic enzymes, actinomycetes have been singled out for the vast diversity of other bioactive secondary metabolites they produce. (Bérdy, 2005). *Micromonospora*, a genus of actinomycetes, has been identified as an important player in soil ecology through the production of bioactive metabolites including hormones and antibiotics (Genilloud et al., 2010; Hirsch and Valdés, 2010), as well as other more direct relationships with plants such as inducing systemic resistance (Martínez-Hidalgo et al. 2015). Despite these developments, there remains a need for identification of specific strains of *Micromonospora* species, as well as of species of other genera, that are effective at promoting plant growth. While it is known that some *Micromonospora* bacteria may have plant-growth promoting effects, the correct selection of specific strains is essential. The same is true for other genera of bacteria.

SUMMARY OF THE INVENTION

In order to meet these needs, the present disclosure provides novel microbial isolates, combinations of such isolates, compositions containing such isolates, and methods of using such isolates for increasing plant growth characteristics in plants.

In some embodiments disclosed herein, there is disclosed a method of increasing one or more plant growth characteristics in a plant, the method comprising: providing to the plant an effective amount of one or more of the following plant growth-promoting microbial isolates: *Variovorax* 2u118, *Ochrobactrum* 1u19, *Ochrobactrum* 2u13, *Ochrobactrum* 2u114, *Ochrobactrum* 2u24, *Bacillus* 1u117, *Bacillus* PSB43' (NRRL Accession No. B-67416, deposited Apr. 5, 2017), *Bacillus* 1SD10, *Bacillus* PSB33, *Bacillus* PSB32, *Bacillus* PSCA15, *Bacillus* 15Sd13, *Bacillus* USAFON2, *Bacillus* 1SB6, *Bacillus* 1SA (ca) 5, *Bacillus* 1SD11, *Bacillus* 1SB5, *Bacillus* PSCA21, *Bacillus* USAFOC6, *Bacillus* USAFONa 16, *Oceanobacillus* UTRUM2, *Paenibacillus* USAFONa6, *Micromonospora* USAFONa4, *Micromonospora* UTRUM1 (NRRL Accession No. B-67418, deposited Apr. 5, 2017), *Pseudonocardia* 2u210, *Streptomyces* USAFOC17, *Streptomyces* USAFOC20, *Ensifer* 1u 10, *Ensifer* 1u111, *Ensifer* 1u113, *Ensifer* 1u114, *Ensifer* 1u115, *Ensifer* 1u116, *Ensifer* 2u110, *Ensifer* 2u15, *Ensifer* 2u16, *Ensifer* 2u17, *Ensifer* 2u18, *Ensifer* 2u27, *Ensifer* 4650D, *Ensifer* 4650F, *Ensifer* 4677A, *Ensifer* USAF16, *Ensifer* USAF17, *Ensifer* 2S (ca) 3, *Ensifer* PSB71, *Ensifer* USAF6, *Ensifer* 1u118, *Ensifer* USAF1, *Ensifer* USAFON1, *Rhizobium* 1u112a, 1SB12, 1SB7, 1SD9, 1u24b, 2S(Ca)4, 2S4, 2u111, 2u112, PSB30, PSB36, PSB43, PSB72, PSB74, PSCa18, PSCA25, PSCA26, PSCa3, USAF29PDA, USAFOC, USAFOC8, USAFON3, *Onithinibacillus* utrum1', *Paenibacillus pabuli* 151 (NRRL Accession No. B-67417, deposited Apr. 5, 2017), *Dietzia cinnamea* 55 (NRRL Accession No. B-67422, deposited Apr. 5, 2017), *Lysinobacillus sphaericus* 47 (NRRL Accession No. B-67423, deposited Apr. 5, 2017), *Paenibacillus* MBEV37 B17 (Accession No. B-67419, deposited Apr. 5, 2019), *Exiguobacterium alkaliphilum* 20 (NRRL Accession No. B-67425, deposited Apr. 5, 2017), *Paenibacillus tundrae* 47' (NRRL Accession No. B-67420, deposited Apr. 5, 2017), *Bacillus simplex* 237 (NRRL Accession No. B-67421, deposited Apr. 5, 2017), and *Bacillus safensis* (NRRL Accession No. B-67620, deposited May 11, 2018). In referring to the individual microbial isolates herein, the genus name, such as *Micromonospora, Bacillus,* or *Ensifer,* is sometimes given along with the strain designation, such as 2u13 or USAFOC6. The genus designation is based on comparison of 16S rRNA sequences to known microbial species, as described further in the Examples below, and is not meant to be limiting. The microbial isolates disclosed herein have all the identifying characteristics of deposited microorganisms having the same strain designation as those used herein and/or having the indicated accession numbers. Any number of these microbial isolates can be used in the methods described herein, including one or more, two or more, three or more, four or more, five or more, six or more, seven or more, eight or more, nine or more, 10 or more, 15 or more, 20 or more, 25 or more, 30 or more, 35 or more, 40 or more, 45 or more, 50 or more, 55 or more, 60 or more, 65 or more, or 70 or more of the plant growth-promoting microbial isolates, or any range between any two of these values. In some embodiments, the one or more plant growth-promoting microbial isolates comprises *Bacillus* PSB43' (NRRL Accession No. B-67416). In some embodiments, the one or more plant growth-promoting microbial isolates comprises *Micromonospora* UTRUM1 (NRRL Accession No. B-67418). In some embodiments, the one or more plan growth-promoting microbial isolates comprises *Bacillus safensis* 34 (NRRL Accession No. B-67620). In some embodiments, the one or more plant growth-promoting microbial isolates comprises *Micromonospora* USAFONa4.

In some embodiments, the microbial isolates used in the methods and compositions disclosed herein have one or more of the following abilities: nitrogen fixation, siderophore production, iron chelation, phosphate solubilization, chitinase production, cellulase production, pectinase production, xylanase production, growth at pH 4.5, growth at pH 5.5, and growth in 5% NaCl.

The microbial isolates disclosed herein may promote plant growth in a number of ways. In some embodiments, a method of promoting one or more plant growth characteristics comprises promoting one or more of the following characteristics: plant biomass, plant growth rate, plant yield, shoot length, shoot biomass, fresh cob weight, dry cob weight, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and growth under high temperature soil conditions. Other plant growth characteristics may also be promoted using the microbial isolates disclosed herein.

In some embodiments of methods of promoting one or more plant growth characteristics, the microbial isolates disclosed herein may be provided in combination with other microbes. In some embodiments, the plant is provided an effective amount of one or more rhizobial bacterial strains in addition to the strains described above. In some embodiments, the one or more rhizobial bacterial strains comprises *Ensifer meliloti* 1021. In some embodiments, a combination of strains exhibits an additive or synergistic effect in promoting a plant growth characteristic. When provided in combination with another strain, the microbial isolates disclosed herein may be provided together with the additional strains. This may be achieved by mixing the strains in a single composition or by providing the strains in separate compositions at approximately the same time. Providing the strains in combination may also entail providing one or more of the strains described above before or after another strain, but in close enough succession that the strains can exert a combined effect on one or more plant growth promoting characteristics.

In some embodiments providing to the plant an effective amount of one or more of the plant growth-promoting microbial isolates promotes one or more plant growth characteristics better than *Ensifer meliloti* 1021. In some embodiments, providing to the plant an effective amount of one or more of the plant growth-promoting microbial isolates in combination with *Ensifer meliloti* 1021 or another rhizobial bacterial strain promotes one or more plant growth characteristics more effectively than than *Ensifer meliloti* 1021 or another rhizobial bacterial strain without the composition.

Providing a plant with one or more plant growth-promoting microbial isolates can be accomplished in a variety of ways known to those skilled in the art. In some embodiments, providing to the plant an effective amount of one or more plant growth-promoting microbial isolates comprises contacting seed of the plant with the one or more plant growth-promoting microbial isolates. In some embodiments, providing to the plant an effective amount of one or more plant growth-promoting microbial isolates comprises adding the one or more plant growth-promoting microbial isolates to the soil in which the plant is growing or will grow. In some embodiments, providing to the plant an effective amount of one or more plant growth-promoting microbial isolates comprises contacting the plant or a part thereof with the one or more plant growth-promoting microbial isolates. Contacting the plant may be effective when one or more of various plant parts are contacted with the microbial isolates. In some embodiments, the plant part comprises the plant roots. In some embodiments, the plant part comprises the plant rhizosphere. The rhizosphere may comprise one or more of roots, root nodules, root caps, root exudate, rhizosphere-associate microorganisms, and rhizosphere-associated soil.

The plants whose one or more growth characteristics may be promoted according to methods disclosed herein include many varieties of plants. In some embodiments, the plant is a dicotyledon, a crop plant, and/or a legume.

Also disclosed herein is a composition comprising one or more microbial isolates selected from the following: *Variovorax* 2u118, *Ochrobactrum* 1u19, *Ochrobactrum* 2u13, *Ochrobactrum* 2u114, *Ochrobactrum* 2u24, *Bacillus* 1u117, *Bacillus* PSB43', *Bacillus* 1SD10, *Bacillus* PSB33, *Bacillus* PSB32, *Bacillus* PSCA15, *Bacillus* 15Sd13, *Bacillus*

USAFON2, *Bacillus* 1SB6, *Bacillus* 1SA (ca) 5, *Bacillus* 1SD11, *Bacillus* 1SB5, *Bacillus* PSCA21, *Bacillus* USAFOC6, *Bacillus* USAFONa16, *Oceanobacillus* UTRUM2, *Paenibacillus* USAFONa6, *Micromonospora* USAFONa4, *Micromonospora* UTRUM1, *Pseudonocardia* 2u210, *Streptomyces* USAFOC17, *Streptomyces* USAFOC20, *Ensifer* 1u10, *Ensifer* 1u111, *Ensifer* 1u113, *Ensifer* 1u114, *Ensifer* 1u115, *Ensifer* 1u116, *Ensifer* 2u110, *Ensifer* 2u15, *Ensifer* 2u16, *Ensifer* 2u17, *Ensifer* 2u18, *Ensifer* 2u27, *Ensifer* 4650D, *Ensifer* 4650F, *Ensifer* 4677A, *Ensifer* USAF16, *Ensifer* USAF17, *Ensifer* 2S (ca) 3, *Ensifer* PSB71, *Ensifer* USAF6, *Ensifer* 1u118, *Ensifer* USAF1, *Ensifer* USAFON1, *Rhizobium* 1u112a, 1SB12, 1SB7, 1SD9, 1u24b, 2S(Ca)4, 2S4, 2u111, 2u112, PSB30, PSB36, PSB43, PSB72, PSB74, PSCa18, PSCA25, PSCA26, PSCa3, USAF29PDA, USAFOC, USAFOC8, USAFON3, *Onithinibacillus* utrum1', *Paenibacillus pabuli* 151, *Dietzia cinnamea* 55, *Lysinobacillus sphaericus* 47, *Paenibacillus* MBEV37 B17, *Exiguobacterium alkaliphilum* 20, *Paenibacillus tundrae* 47', *Bacillus simplex* 237, and *Bacillus safensis* 34. In some embodiments, the composition is a plant growth-promoting composition. In some embodiments, the one or more microbial isolates are plant growth-promoting microbial isolates. In some embodiments, the composition comprises an effective amount of the one or more microbial isolates. In some embodiments, the composition comprises one or more, two or more, three or more, four or more, five or more, six or more, seven or more, eight or more, nine or more, 10 or more, 15 or more, 20 or more, 25 or more, 30 or more, 35 or more, 40 or more, 45 or more, 50 or more, 55 or more, 60 or more, 65 or more, or 70 or more of the plant growth-promoting microbial isolates, or any range between any two of these values. In some embodiments, the one or more plant growth-promoting microbial isolates comprises *Bacillus* PSB43'. In some embodiments, the one or more plant growth-promoting microbial isolates comprises *Micromonospora* UTRUM1. In some embodiments, the one or more plant growth-promoting microbial isolates comprises *Micromonospora* USAFONa4. In some embodiments, the plant-growth promoting microbial isolates have one or more of the following abilities: nitrogen fixation, siderophore production, iron chelation, phosphate solubilization, chitinase production, cellulase production, pectinase production, xylanase production, growth at pH 4.5, growth at pH 5.5, and growth in 5% NaCl. In some embodiments, the composition comprises an amount of one or more microbial isolates that is effective to promote one of the following plant growth characteristics: plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and growth under high temperature soil conditions.

In some embodiments, the compositions comprising one or more of the microbial isolates disclosed herein comprise additional substances that affect the properties of the microbial isolate(s) in the composition. Such substances may include mannitol, skim milk, bovine serum albumin (BSA), sucrose, and/or trehalose. Mannitol, skim milk, BSA, plant protein, and other similar agents can be used to give body to a bacterial suspension after freeze drying. Sucrose, trehalose, glycerol, and other lysoprotectants alter the ability of bacteria in the composition to survive freezing, which may be done as part of a freeze drying process. In some embodiments, the composition comprises aqueous solutions comprising 5-10% sucrose, trehalose, or glycerol. In some embodiments, the microbial isolate is comprised in a freeze dried composition.

In some embodiments, the compositions disclosed herein comprise additional substances. In some embodiments, the composition comprises plant seeds. In some embodiments, the composition comprises one or more additional microbial strains, such as a rhizobial bacterial strain. In some embodiments, the rhizobial bacterial strain is *Ensifer meliloti* 1021.

In some embodiments, the composition has the ability to promote one or more plant growth characteristics better than *Ensifer meliloti* 1021. In some embodiments, the combination of the composition with *Ensifer meliloti* 1021 or another rhizobial bacterial strain has the ability to promote one or more plant growth characteristics more effectively than *Ensifer meliloti* 1021 or another rhizobial bacterial strain without the composition.

Also disclosed herein are isolated bacteria capable of increasing one or more plant growth characteristics in a plant and comprising bacteria of at least one bacterial strain having all the identifying characteristics of an isolate selected from the following: *Variovorax* 2u118, *Ochrobactrum* 1u19, *Ochrobactrum* 2u13, *Ochrobactrum* 2u114, *Ochrobactrum* 2u24, *Bacillus* 1u117, *Bacillus* PSB43', *Bacillus* 1SD10, *Bacillus* PSB33, *Bacillus* PSB32, *Bacillus* PSCA15, *Bacillus* 15Sd13, *Bacillus* USAFON2, *Bacillus* 1SB6, *Bacillus* 1SA (ca) 5, *Bacillus* 1SD11, *Bacillus* 1SB5, *Bacillus* PSCA21, *Bacillus* USAFOC6, *Bacillus* USAFONa16, *Oceanobacillus* UTRUM2, *Paenibacillus* USAFONa6, *Micromonospora* USAFONa4, *Micromonospora* UTRUM1, *Pseudonocardia* 2u210, *Streptomyces* USAFOC17, *Streptomyces* USAFOC20, *Ensifer* 1u10, *Ensifer* 1u111, *Ensifer* 1u113, *Ensifer* 1u114, *Ensifer* 1u115, *Ensifer* 1u116, *Ensifer* 2u110, *Ensifer* 2u15, *Ensifer* 2u16, *Ensifer* 2u17, *Ensifer* 2u18, *Ensifer* 2u27, *Ensifer* 4650D, *Ensifer* 4650F, *Ensifer* 4677A, *Ensifer* USAF16, *Ensifer* USAF17, *Ensifer* 2S (ca) 3, *Ensifer* PSB71, *Ensifer* USAF6, *Ensifer* 1u118, *Ensifer* USAF1, *Ensifer* USAFON1, *Rhizobium* 1u112a, 1SB12, 1SB7, 1SD9, 1u24b, 2S(Ca)4, 2S4, 2u111, 2u112, PSB30, PSB36, PSB43, PSB72, PSB74, PSCa18, PSCA25, PSCA26, PSCa3, USAF29PDA, USAFOC, USAFOC8, USAFON3, *Onithinibacillus* utrum1', and *Bacillus safensis* 34.

Also disclosed herein is an isolated bacterial strain having all the identifying characteristics of a *Bacillus* PSB43' strain deposited with NRRL as Accession No. B-67416. Also disclosed herein is an isolated bacterial strain having all the identifying characteristics of a *Micromonospora* UTRUM1 strain deposited with NRRL as Accession No. B-67418. Also disclosed herein is an isolated bacterial strain having all the identifying characteristics of a *Micromonospora* USAFONa4 strain. Also disclosed herein is an isolated bacterial strain having all the identifying characteristics of a *Paenibacillus pabuli* 151 strain deposited with NRRL as Accession No. B-67417. Also disclosed herein is an isolated bacterial strain having all the identifying characteristics of a *Dietzia cinnamea* 55 strain deposited with NRRL as Accession No. B-67422. Also disclosed herein is an isolated bacterial strain having all the identifying characteristics of a *Lysinobacillus sphaericus* 47 strain deposited with NRRL as Accession No. B-67423. Also disclosed herein is an isolated bacterial strain having all the identifying characteristics of a *Paenibacillus* MBEV37 B17 strain deposited with NRRL as Accession No. B-67419. Also disclosed herein is an isolated bacterial strain having all the identifying characteristics of an *Exiguobacterium alkaliphilum* 20 strain deposited with NRRL as Accession No. B-67425. Also disclosed herein is an isolated bacterial strain having all the identifying characteristics of a *Paenibacillus tundrae* 47' strain deposited with NRRL as Accession No. B-67420. Also disclosed herein is an isolated bacterial strain having all the identifying characteristics of a *Bacillus simplex* 237 strain deposited with NRRL as Accession No. B-67421. Also disclosed herein is an isolated bacterial strain having all the identifying characteristics of a *Bacillus safensis* 34 strain deposited with the NRRL as Accession No. B-67620.

Also disclosed is a method of increasing one or more plant growth characteristics comprising contacting a plant or part thereof with *Dietzia cinnamea* 55 (NRRL Accession No. B-67422). In some embodiments, the plant is corn. In some embodiments, contacting the plant or part thereof comprises contacting the seeds with *Dietzia cinnamea* 55. In some embodiments, contacting the seeds with *Dietzia cinnamea* 55 comprises placing the seeds in a broth culture of *Dietzia cinnamea* 55.

An "effective amount" as used herein refers to the amount of an agent, such as a microbe, or combined amounts of multiple agents that, when applied to or otherwise provided to a plant, a seed, or portion of a plant, is sufficient to enhance a plant growth characteristic of the plant Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is specifically contemplated that embodiments described herein may be excluded. It is further contemplated that, when a range is described, certain ranges may be excluded.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Throughout this application, the term "about" is used to indicate that a value includes the inherent variation of error for the device, the method being employed to determine the value, or the variation that exists among the study subjects. Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 5A-5B. In vitro phenotypic assays. CAS, siderophore production; CMC, cellulose degradation; C source CMC, cellulose as the sole carbon source; C source pectin, pectin as the sole carbon source; pH4.5-pH9, tolerance to different pH values; N-free medium, growth on nitrogen-free medium; P solubilization, PVK phosphate solubilization; C source xylan, xylan as a carbon source; NaCl 1-5%, halotolerance; casein, protease activity. Degree of positive and negative phenotypes indicated by +/−. The "?" symbol indicates ambiguous results. Unavailable data indicated by "na."

DESCRIPTION OF ILLUSTRATIVE EMBODIMENTS

Figure 1:
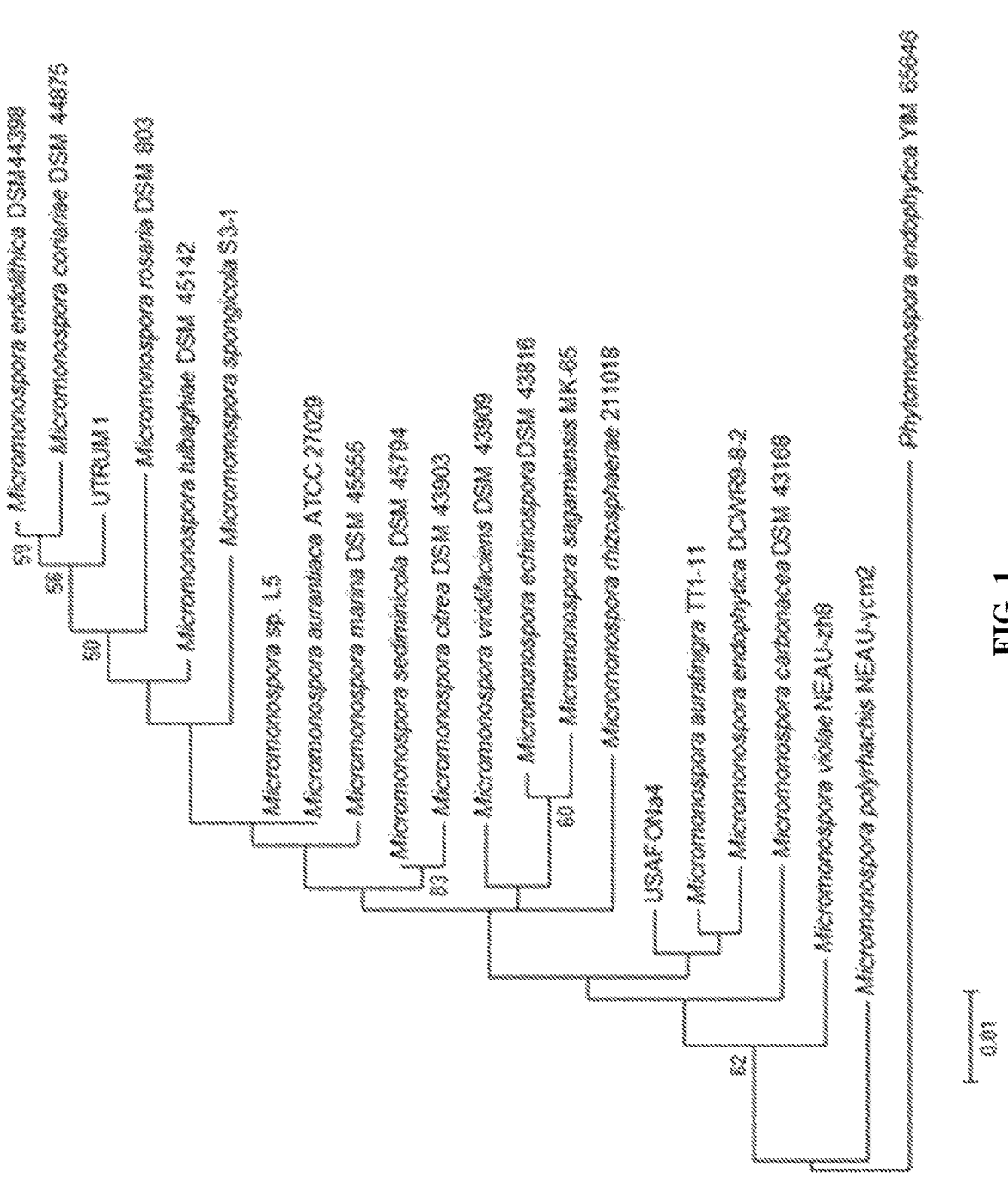
FIG. 1. Maximum likelihood phylogenetic tree of *Micromonospora* bacteria isolated from *Medicago truncatula* based on 16S rRNA gene sequences showing the relationship between the *Micromonospora* isolates and the closest recognized *Micromonospora* species. Bar, 0.01 substitutions per nucleotide position. Boostrap percentages (1000 replicates) above 50% are shown at nodes.

Disclosed herein are plant growth promoting microbial isolates, including those that have been isolated from *Medicago* root nodules, as well as compositions including such isolates and methods of using such isolates. These and other aspects of the disclosure are described in more detail below.

The present disclosure provides methods and compositions for use in increasing one or more plant growth characteristics by providing the plant with or growing the plant in the presence of one or more plant growth-promoting microbial isolates of the present disclosure. As used herein, "plant growth-promoting microbial isolate(s)," "PGPM isolate(s)," and "plant growth-promoting microorganism(s)" refer to isolated microbial strains, such as prokaryotes (e.g., bacteria), fungi, yeast, and the like, that are beneficial to plants. For example, such "PGPM isolate(s)" may exhibit characteristics including, without limitation, nitrogen fixation, siderophore production, iron chelation, phosphate solubilization, chitinase production, and cellulase production, that promote plant growth by increasing one or more plant growth characteristics. As used herein "plant growth characteristic(s)" refers to any plant trait associated, for example, with plant growth, development, hardiness, and yield.

I. PLANT GROWTH-PROMOTING MICROBIAL ISOLATES

Certain aspects of the present disclosure are related to compositions including one or more isolated plant growth-promoting microorganisms (e.g., microbial isolates) and methods of using such compositions for increasing one or more plant growth characteristics in plants. Any growth-promoting microorganisms may be used to increase plant growth characteristics in plants. Advantageously, microbial isolates of the present disclosure have one or more plant growth-promoting (PGP) activities that allow plants to grow in harsh environments, such as high salt environments, high or low pH environments, low moisture environments, deserts, arid environments, nitrogen-poor environments, nutrient-poor environments, low temperature environments, and high temperature environments. For example, microbial isolates of the present disclosure may exhibit characteristics including, without limitation, nitrogen fixation, siderophore production, iron chelation, phosphate solubilization, chitinase production, and cellulase production, that promote plant growth in plants grown under harsh environments or in favorable environments. PGPM isolates of the present disclosure include, without limitation, bacteria, such as actinomycetes, firmicutes, and proteobacteria; archaea; fungi; and yeast.

Suitable PGPM isolates of the present disclosure include, without limitation, any PGPMs isolated from the plant tissue, seeds, roots, rhizosphere, plant-associated soil samples, and/or surrounding soil samples from indigenous plants that grow in harsh environmental conditions, such as deserts, arid environments, nitrogen-poor environments, nutrient-poor environments, low pH environments, high pH environments, low temperature environments, and high temperature environments, or from plants that grow in favorable environments. Accordingly, in some embodiments, PGPM isolates of the present disclosure, exhibit one or more characteristics that include, without limitation, nitrogen fixation, siderophore production, iron chelation, phosphate solubilization, chitinase production, and cellulase production.

In certain embodiments, plant growth-promoting microbial (PGPM) isolates of the present disclosure include, without limitation, any PGPM isolated from the plant tissue, seeds, roots, rhizosphere, plant-associated soil samples, and/or surrounding soil samples from *Medicago* plants, including *Medicago truncatula* and *Medicago sativa*. In some embodiments, the PGPM isolates are isolated from root nodules of *Medicago* plants. In some embodiments, the PGPM isolates are isolated from surface-sterilized root nodules of *Medicago* plants. In some embodiments, the PGPM are isolated using bacterial culture-dependent methods, including trap experiments.

Examples of suitable PGPM isolates of the present disclosure include, without limitation, those listed in Table 1.

TABLE 1

| Strain Designation (including genus where available) | NRRL Accession No. |
|---|---|
| *Variovorax* sp. 2u118 | |
| *Ochrobactrum* sp. 1u19 | |
| *Ochrobactrum* sp. 2u13 | |
| *Ochrobactrum* sp. 2u114 | |
| *Ochrobactrum* sp. 2u24 | |
| *Bacillus* sp. 1u117 | |
| *Bacillus* sp. PSB43' | B-67416 |
| *Bacillus* sp. 1SD10 | |
| *Bacillus* sp. PSB33 | |
| *Bacillus* sp. PSB32 | |
| *Bacillus* sp. PSCA15 | |
| *Bacillus* sp. 15Sd13 | |
| *Bacillus* sp. USAFON2 | |
| *Bacillus* sp. 1SB6 | |
| *Bacillus* sp. 1SA(ca)5 | |
| *Bacillus* sp. 1SD11 | |
| *Bacillus* sp. 1SB5 | |
| *Bacillus* sp. PSCA21 | |
| *Bacillus* sp. USAFOC6 | |
| *Bacillus* sp. USAFONa16 | |
| *Oceanobacillus* sp. UTRUM2 | |
| *Paenibacillus* sp. USAFONa6 | |
| *Micromonospora* sp. USAFONa4 | |
| *Micromonospora* sp. UTRUM1 | B-67418 |
| *Pseudonocardia* sp. 2u210 | |
| *Streptomyces* sp. USAFOC17 | |
| *Streptomyces* sp. USAFOC20 | |
| *Ensifer* sp. 1u10 | |
| *Ensifer* sp. 1u111 | |
| *Ensifer* sp. 1u113 | |
| *Ensifer* sp. 1u114 | |
| *Ensifer* sp. 1u115 | |
| *Ensifer* sp. 1u116 | |
| *Ensifer* sp. 2u110 | |
| *Ensifer* sp. 2u15 | |
| *Ensifer* sp. 2u16 | |
| *Ensifer* sp. 2u17 | |
| *Ensifer* sp. 2u18 | |
| *Ensifer* sp. 2u27 | |
| *Ensifer* sp. 4650D | |
| *Ensifer* sp. 4650F | |
| *Ensifer* sp. 4677A | |
| *Ensifer* sp. USAF16 | |
| *Ensifer* sp. USAF17 | |
| *Ensifer* sp. 2S(ca)3 | |
| *Ensifer* sp. PSB71 | |
| *Ensifer* sp. USAF6 | |
| *Ensifer* sp. 1u118 | |
| *Ensifer* sp. USAF 1 | |
| *Ensifer* sp. USAFON 1 | |
| *Rhizobium* sp. 1u112a | |
| 1SB12 | |

TABLE 1-continued

| Strain Designation (including genus where available) | NRRL Accession No. |
|---|---|
| 1SB7 | |
| 1SD9 | |
| 1u24b | |
| 2S(Ca)4 | |
| 2S4 | |
| 2u111 | |
| 2u112 | |
| PSB30 | |
| PSB36 | |
| PSB43 | |
| PSB72 | |
| PSB74 | |
| PSCa18 | |
| PSCa25 | |
| PSCA26 | |
| PSCa3 | |
| USAF29PDA | |
| USAFOC | |
| USAFOC8 | |
| USAFON3 | |
| Ornithinibacillus sp. utrum1' | |
| Paenibacillus pabuli 151 | B-67417 |
| Dietzia cinnamea 55 | B-67422 |
| Lysinobacillus sphaericus 47 | B-67423 |
| Paenibacillus MBEV37 B17 | B-67419 |
| Exiguobacterium alkaliphilum 20 | B-67425 |
| Paenibacillus tundrae 47' | B-67420 |
| Bacillus simplex 237 | B-67421 |
| Bacillus safensis 34 | B-67620 |

Accordingly, in certain embodiments, the PGPM isolate is an isolated strain having all the identifying characteristics of one of the above-listed strains deposited with the NRRL as Accession Nos. B-67416 to B-674123, B-67425, or B-67620.

In some embodiments, PGPM isolates of the present disclosure also include homologues, variants, and mutants of the PGPM isolates listed in Table 1. Preferably, the homologues, variants, and mutants of the PGPM isolates listed in Table 1 have all the identifying characteristics of the PGPM isolates listed in Table 1.

II. MICROBIAL CONSORTIA

In some embodiments, the plant growth-promoting compositions of the present disclosure include consortia of PGPM isolates having a mixture of two or more PGPM isolates of the present disclosure. A microbial consortium of the present disclosure may be isolated from an environmental sample such as a plant, rhizosphere, or soil sample from a Medicago plant. In addition, a microbial consortium of the present disclosure may be rationally designed by combining microbial strains, such as the PGPM isolates of the present disclosure. Moreover, microbial consortia of the present disclosure may further include one or more rhizobial bacterial strains in addition to any of the microbial strains disclosed herein. Any suitable rhizobial strain known in the art may be used.

Accordingly, in certain embodiments, a plant of the present disclosure is grown in the presence of a microbial consortium containing from two or more to 70 or more PGPM isolates of the present disclosure. In some embodiments, a plant of the present disclosure is grown in the presence of a microbial consortium containing two or more, three or more, four or more, five or more, six or more, seven or more, eight or more, nine or more, 10 or more, 15 or more, 20 or more, 25 or more, 30 or more, 35 or more, 40 or more, 45 or more, 50 or more, 55 or more, 60 or more, 65 or more, 70 or more, or 75 or more of the PGPM isolates of the present disclosure.

III. PLANT GROWTH-PROMOTING COMPOSITIONS

Other aspects of the present disclosure relate to plant growth-promoting (PGP) compositions containing one or more PGPM isolates of the present disclosure for increasing one or more plant growth characteristics in plants.

In some embodiments, the PGP composition may include from one or more to 70 or more PGPM isolates of the present disclosure. In other embodiments, the PGP composition includes one or more, two or more, three or more, four or more, five or more, six or more, seven or more, eight or more, nine or more, 10 or more, 15 or more, 20 or more, 25 or more, 30 or more, 35 or more, 40 or more, 45 or more, 50 or more, 55 or more, 60 or more, 65 or more, or 70 or more of the PGPM isolates of the present disclosure.

In certain embodiments, the PGP composition may also include one or more rhizobial bacterial strains in addition to the PGPM isolates of the present disclosure. Any suitable rhizobial strain known in the art may be used, including Ensifer meliloti 1021.

In order to achieve an increase in one or more plant growth characteristics, the PGP compositions of the present disclosure may also include other components or mixture of components to facilitate the viability of the PGPM isolates; inoculation of the plant, plant parts thereof, or rhizospheres; or transportation or storage of the compositions. Any suitable components known in the art may be used.

In some embodiments, the PGP compositions of the present disclosure may further contain a carrier for delivering, inoculating, or otherwise growing a plant in the presence of the composition in order to promote plant growth and productivity, such as germination, yield, and the like, by increasing one or more plant growth characteristics. Any suitable carrier known in the art may be used, including without limitation, a liquid, a solid, and a combination of a liquid and a solid carrier. In some embodiments, the liquid carrier may include water.

PGP compositions of the present disclosure may further contain components for providing additional benefits to the PGPM isolates or plants, including without limitation, an herbicide, a pesticide, a fungicide, a plant growth regulator, and an encapsulation agent, a wetting agent, a dispersing agent, and the like for enhancing the effect of the PGP composition.

IV. PLANTS

Other aspects of the present disclosure relate to growing plants in the presence of one or more PGPM isolates of the present disclosure in order to increase one or more plant growth characteristics in the plant.

Plants of the present disclosure may be of any kind or from any source known in the art. For example, suitable plants of the present disclosure include, without limitation, those intended to be grown in harsh environments, such as plants grown in soils that are dry, acidic, or both; plants that are prone to infection by pathogens, such as fungi; plants grown in a desert or arid environment; plants grown in nitrogen-poor environments; plants grown in nutrient-poor environments; plants grown in low pH conditions; plants grown in high pH conditions; plants grown in low temperature conditions; and plants grown in high temperature conditions. Suitable plants of the present disclosure may be native to such harsh environments, or may plants grown in harsh environments but that are not native to such harsh environments. Suitable plants used with the compositions and methods of the present disclosure may be grown in any environment or in any growth medium, such as solid medium or liquid medium. Suitable plants of the present disclosure may also include plants that are grown in favorable conditions.

Suitable plants of the present disclosure include, without limitation, crop plants, energy crop plants, plants that are used in agriculture, and plants used in industrial settings. Plants of the present disclosure may be either monocotyledons or dicotyledons. For example, suitable plants of the present disclosure include, without limitation, desert plants, desert perennials, legumes, such as *Medicago sativa*, (alfalfa), *Lotus japonicus, Melilotus alba* (sweet clover), *Pisum sativum* (pea), and *Vigna unguiculata* (cowpea), *Mimosa pudica, Lupinus succulentus* (lupine), *Macroptilium atropurpureum* (siratro), *Medicago truncatula*, and *Trifolium repens* (white clover), corn, sorghum, *miscanthus*, sugarcane, poplar, spruce, pine, wheat, rice, soy, cotton, barley, turf grass, tobacco, potato, bamboo, rape, sugar beet, sunflower, willow, *Eucalyptus, Amorphophallus* spp., *Amorphophallus konjac*, giant reed (*Arundo donax*), reed canary-grass (*Phalaris arundinacea*), *Miscanthus giganteus, Miscanthus* sp., *sericea lespedeza* (*Lespedeza cuneata*), millet, ryegrass (*Lolium multiflorum, Lolium* sp.), timothy, *Kochia* (*Kochia scoparia*), forage soybeans, clover, sunn hemp, kenaf, bahiagrass, bermudagrass, dallisgrass, pangolagrass, big bluestem, indiangrass, fescue (*Festuca* sp.), *Dactylis* sp., Brachypodium distachyon, smooth bromegrass, orchardgrass, and Kentucky bluegrass.

In certain embodiments, the plants are dicotyledons. It will be apparent to one of skill in the art that the plants of the present disclosure may also include nodulating plants. In other embodiments, the plants are desert plants, desert perennials, crop plants, or legumes. In certain embodiments, the plant are legumes, including without limitation, *Medicago sativa*, (alfalfa), *Lotus japonicus, Melilotus alba* (sweet clover), *Pisum sativum* (pea), and *Vigna unguiculata* (cowpea), *Mimosa pudica, Lupinus succulentus* (lupine), *Macroptilium atropurpureum* (siratro), *Medicago truncatula* and *Trifolium repens* (white clover).

V. PLANT GROWTH CHARACTERISTICS

In some embodiments, PGPM isolates of the present disclosure increase one or more plant growth characteristics of plants of the present disclosure. Plant growth characteristics of the present disclosure include, without limitation, plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and growth under high temperature soil conditions. As will be apparent to one of skill in the art, certain characteristics, for example nodulation, include other forms of life that interact with the plant.

As used herein, "increasing one or more plant growth characteristic" refers to increasing, without limitation, plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and growth under high temperature soil conditions of a plant grown in the presence of one or more PGPM isolates of the present disclosure, as compared to a corresponding plant grown under the same conditions but in the absence of the one or more PGPM isolates of the present disclosure.

In certain embodiments, growing a plant in the presence of one or more PGPM isolates of the present disclosure increases, without limitation, plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and/or growth under high temperature soil conditions by about 5% to about 200%, as compared to a corresponding plant grown under the same conditions but in the absence of the one or more PGPM isolates of the present disclosure. In some embodiments, growing a plant in the presence of one or more PGPM isolates of the present disclosure increases, without limitation, plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and/or growth under high temperature soil conditions by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, or about 200%, or by a range between any two of these values, as compared to a corresponding plant grown under the same conditions but in the absence of the one or more PGPM isolates of the present disclosure.

In other embodiments, growing a plant in the presence of one or more PGPM isolates of the present disclosure increases, without limitation, plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and/or growth under high temperature soil conditions by about 2-fold to about 100-fold, as compared to a corresponding plant grown under the same conditions but in the absence of the one or more PGPM isolates of the present disclosure. In some embodiments, growing a plant in the presence of one or more PGPM isolates of the present disclosure increases, without limitation, plant biomass, plant growth rate, plant yield, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and/or growth under high temperature soil conditions by about 2-fold, about 2.5-fold, about 3-fold, about 3.5-fold, about 4-fold, about 4.5-fold, about 5-fold, about 5.5-fold, about 6-fold, about 6.5-fold, about 7-fold, about 7.5-fold, about 8-fold, about 8.5-fold, about 9-fold, about 9.5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, or about 100-fold, or by an amount between any two of these values, as compared to a corresponding plant grown under the same conditions but in the absence of the one or more PGPM isolates of the present disclosure.

As disclosed herein, plant biomass and yield refer to the accumulation of plant matter in any part or all of the plant, with yield including, without limitation, the crop production of crop plants.

As disclosed herein, nodulation includes any process or quality associated with root nodule formation, including but not limited to nodule size, color, clustering, development, branching of vascular bundles, and colonization by *rhizobia*.

As disclosed herein, nitrogen and nutrient utilization include, without limitation, how well nitrogen or nutrients are taken up by the plant, the amounts of nitrogen or nutrients present in the plant, tissues thereof, or surrounding soil environment, and/or how efficiently the nitrogen or nutrients are incorporated or utilized by the plant.

As disclosed herein, resistance to pathogens or fungal growth includes, without limitation, increased plant survival upon infection with pathogen or fungal growth, a decreased growth rate or size of pathogen or fungal growth on or near the plant, or a diminished frequency with which pathogen or fungal growth appears on or near the plant.

As disclosed herein, arid conditions and arid soil conditions refer to any environment in which the plant and its immediate surroundings receive less than 50 mm of water per month. Arid conditions and arid soil conditions may also refer to any environment characterized by irregular exposure of plants to water, regardless of the total amount received.

As disclosed herein, low pH conditions and low pH soil conditions refer to any environment for plant growth with a pH of between about 0.0 to about 6.0, for example about 0.0, about 0.5, about 1.0, about 1.5, about 2.0, about 2.5, about 3.0, about 3.5, about 4.0, about 4.5, about 5.0, about 5.1, about 5.2, about 5.3, about 5.4, about 5.5, about 5.6, about 5.7, about 5.8, about 5.9, or about 6.0, or below any of these values, or between any two of these values. High pH conditions and high pH soil conditions refer to any environment for plant growth with a pH of about 6.1 to about 14, for example about 6.1, about 6.2, about 6.3, about 6.4, about 6.5, about 6.7, about 6.8, about 6.9, about 7.0, about 7.5, about 8.0, about 8.5, about 9.0, about 9.5, about 10, about 10.5, about 11, about 11.5, about 12, about 12.5, about 13, about 13.5, or about 14, or above any of these values, or between any two of these values.

As disclosed herein, low temperature and low temperature soil conditions refer to an ambient or soil temperature less than or equal to 15° C., for example less than or equal to −30° C., less than or equal to −25° C., less than or equal to −20° C., less than or equal to −15° C., less than or equal to −10° C., less than or equal to −9° C., less than or equal to −8° C., less than or equal to −7° C., less than or equal to −6° C., less than or equal to −5° C., less than or equal to −4° C., less than or equal to −3° C., less than or equal to −2° C., less than or equal to −1° C., less than or equal to −0° C., less than or equal to 1° C., less than or equal to 2° C., less than or equal to 3° C., less than or equal to 4° C., less than or equal to 5° C., less than or equal to 6° C., less than or equal to 7° C., less than or equal to 8° C., less than or equal to 9° C., less than or equal to 10° C., less than or equal to 11° C., less than or equal to 12° C., less than or equal to 13° C., less than or equal to 14° C., or less than or equal to 15° C., or less than or equal to any of these values, or between any two of these values. High temperature and high temperature soil conditions refer to an ambient or soil temperature greater than or equal to 50° C., for example greater than or equal to 15° C., greater than or equal to 20° C., greater than or equal to 25° C., greater than or equal to 26° C., greater than or equal to 27° C., greater than or equal to 28° C., greater than or equal to 29° C., greater than or equal to 30° C., greater than or equal to 31° C., greater than or equal to 32° C., greater than or equal to 33° C., greater than or equal to 34° C., greater than or equal to 34° C., greater than or equal to 35° C., greater than or equal to 36° C., greater than or equal to 37° C., greater than or equal to 38° C., greater than or equal to 39° C., greater than or equal to 40° C., greater than or equal to 41° C., greater than or equal to 42° C., greater than or equal to 43° C., greater than or equal to 44° C., greater than or equal to 45° C., greater than or equal to 46° C., greater than or equal to 47° C., greater than or equal to 48° C., greater than or equal to 49° C., or greater than or equal to 50° C., or greater than any of these values or between any two of these values.

VI. CONTACTING AND GROWING PLANTS WITH PLANT GROWTH-PROMOTING MICROBIAL ISOALTES

In some embodiments, plants are grown in the presence of PGPM isolates of the present disclosure. Any suitable method known in the art for growing plants in the presence of microorganisms and disclosed herein may be used. Moreover, any suitable method known in the art for preparing microbial isolates may be used for preparing PGPM isolated of the present disclosure for growing with plants. As disclosed herein, the PGPM isolates may be used in any state or temperature that does not adversely affect the viability of the isolates. For example, the PGPM isolates may be prepared as liquid cultures, lyophilized powders, air-dried powders, freeze-dried powders, beads, spores, aqueous slurries, gums, or prepared within soil or peat preparations.

In certain embodiments, growing a plant in the presence of one or more PGPM isolates of the present disclosure includes contacting the plant, parts thereof, seeds thereof, and/or rhizosphere thereof with one or more PGPM isolates of the present disclosure. Methods of contacting plants, parts thereof, seeds thereof, or rhizosphere thereof with microorganisms are well known in the art, and disclosed herein. Suitable methods may include, without limitation, inoculating the one or more PGPM isolates of the present disclosure into the growth medium of the plant. Exemplary growth media for plants may include, for example, soil and peat.

In some embodiments, growing a plant in the presence of one or more PGPM isolates of the present disclosure includes contacting one or more PGPM isolates of the present disclosure with plant seed. For example, plant seeds may be coated with the one or more PGPM isolates of the present disclosure, in liquid or solid suspensions, directly or in combination with any type of suitable carrier known in the art, including without limitation, any medium, suspension, powder, clay, oil, peat, and the like. Alternatively, the one or more PGPM isolates of the present disclosure may be absorbed into a granular carrier (e.g., pelleted peat) that is planted with the seed.

In other embodiments, growing a plant in the presence of one or more PGPM isolates of the present disclosure includes contacting one or more PGPM isolates of the present disclosure with a plant or part thereof. For example, the one or more PGPM isolates of the present disclosure may be added to any part of the plant, including without limitation, stems, flowers, leaves, nodes, aerial roots, and underground roots, using any suitable method known in the art. The one or more PGPM isolates of the present disclosure may be added at any time during plant growth, or in combination with any other treatment, for example, with fertilizers, pesticides, fungicides, or any combination thereof.

In further embodiments, growing a plant in the presence of one or more PGPM isolates of the present disclosure includes contacting one or more PGPM isolates of the present disclosure with plant roots or the plant rhizosphere. For example, the one or more PGPM isolates of the present disclosure may be encapsulated in beads or in any other carrier and applied to the plant roots or rhizosphere. Alternatively, the one or more PGPM isolates of the present disclosure may be added to the soil or other suitable growth medium containing the rhizosphere using any suitable method known in the art. As used herein, the plant rhizosphere may include, without limitation, roots, root nodules, root caps, root secretions, rhizosphere-associated microorganisms, and rhizosphere-associated soil.

As disclosed herein, the one or more PGPM isolates of the present disclosure may be used at any concentration or dose sufficient to increase one or more plant growth characteristics of a plant that is grown in the presence of such PGPM isolates.

In some embodiments, the plant is also grown in the presences of one or more rhizobial strains. The one or more rhizobial strains may be used in any ratio with the one or more PGPM isolates of the present disclosure that is sufficient to increase one or more plant growth characteristics of a plant that is grown in the presence of the PGPM isolates and rhizobial strains.

VII. DEPOSIT OF MICROORGANISMS

Table 2 lists the deposit strain name of the isolated plant growth-promoting microbial strains of the present disclosure and the NRRL accession number associated with each strain.

TABLE 2

| Strain Designation (including genus where available) | NRRL Accession No. |
|---|---|
| *Variovorax* sp. 2u118 | |
| *Ochrobactrum* sp. 1u19 | |

TABLE 2-continued

| Strain Designation (including genus where available) | NRRL Accession No. |
|---|---|
| *Ochrobactrum* sp. 2u13 | |
| *Ochrobactrum* sp. 2u114 | |
| *Ochrobactrum* sp. 2u24 | |
| *Bacillus* sp. 1u117 | |
| *Bacillus* sp. PSB43' | B-67416 |
| *Bacillus* sp. 1SD10 | |
| *Bacillus* sp. PSB33 | |
| *Bacillus* sp. PSB32 | |
| *Bacillus* sp. PSCA15 | |
| *Bacillus* sp. 15Sd13 | |
| *Bacillus* sp. USAFON2 | |
| *Bacillus* sp. 1SB6 | |
| *Bacillus* sp. 1SA(ca)5 | |
| *Bacillus* sp. 1SD11 | |
| *Bacillus* sp. 1SB5 | |
| *Bacillus* sp. PSCA21 | |
| *Bacillus* sp. USAFOC6 | |
| *Bacillus* sp. USAFONa16 | |
| *Oceanobacillus* sp. UTRUM2 | |
| *Paenibacillus* sp. USAFONa6 | |
| *Micromonospora* sp. USAFONa4 | |
| *Micromonospora* sp. UTRUM1 | B-67418 |
| *Pseudonocardia* sp. 2u210 | |
| *Streptomyces* sp. USAFOC17 | |
| *Streptomyces* sp. USAFOC20 | |
| *Ensifer* sp. 1u10 | |
| *Ensifer* sp. 1u111 | |
| *Ensifer* sp. 1u113 | |
| *Ensifer* sp. 1u114 | |
| *Ensifer* sp. 1u115 | |
| *Ensifer* sp. 1u116 | |
| *Ensifer* sp. 2u110 | |
| *Ensifer* sp. 2u15 | |
| *Ensifer* sp. 2u16 | |
| *Ensifer* sp. 2u17 | |
| *Ensifer* sp. 2u18 | |
| Ensifer sp. 2u27 | |
| *Ensifer* sp. 4650D | |
| *Ensifer* sp. 4650F | |
| *Ensifer* sp. 4677A | |
| *Ensifer* sp. USAF16 | |
| *Ensifer* sp. USAF17 | |
| *Ensifer* sp. 2S(ca)3 | |
| *Ensifer* sp. PSB71 | |
| *Ensifer* sp. USAF6 | |
| *Ensifer* sp. 1u118 | |
| *Ensifer* sp. USAF 1 | |
| *Ensifer* sp. USAFON 1 | |
| *Rhizobium* sp. 1u112a | |
| 1SB12 | |
| 1SB7 | |
| 1SD9 | |
| 1u24b | |
| 2S(Ca)4 | |
| 2S4 | |
| 2u111 | |
| 2u112 | |
| PSB30 | |
| PSB36 | |
| PSB43 | |
| PSB72 | |
| PSB74 | |
| PSCa18 | |
| PSCa25 | |
| PSCA26 | |
| PSCa3 | |
| USAF29PDA | |
| USAFOC | |
| USAFOC8 | |
| USAFON3 | |
| *Ornithinibacillus* sp. utrum1' | |
| *Paenibacillus pabuli* 151 | B-67417 |
| *Dietzia cinnamea* 55 | B-67422 |
| *Lysinobacillus sphaericus* 47 | B-67423 |
| *Paenibacillus* MBEV37 B17 | B-67419 |
| *Exiguobacterium alkaliphilum* 20 | B-67425 |
| *Paenibacillus tundrae* 47' | B-67420 |

TABLE 2-continued

| Strain Designation (including genus where available) | NRRL Accession No. |
| --- | --- |
| *Bacillus simplex* 237 | B-67421 |
| *Bacillus safensis* 34 | B-67620 |

A deposit of each of the isolated microbial strains listed in Table 2 is maintained by The University of California, Los Angeles, having an address at 405 Hilgard Avenue, Los Angeles, Calif. 90095, United States of America. Access to these deposits will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the isolated microbial strains listed in Table 2 will be irrevocably removed by affording access to the isolated microbial strains listed in Table 2 with the Agricultural Research Service Culture Collection, (NRRL), 1815 North University Street, Peoria, Ill., 61604, USA.

The isolated microbial strains listed in Table 2 were deposited on the dates indicated herein in accordance with the Budapest Treaty in the Agricultural Research Service Culture Collection, (NRRL), 1815 North University Street, Peoria, Ill., 61604, USA. The NRRL Accession number assigned for each deposited strain is listed in Table 2. Access to each deposit will be available during the pendency of this application to persons determined by the Commissioner of Patents and Trademarks to be entitled thereto under 37 C.F.R. § 1.14 and 35 U.S.C. § 122. Upon allowance of claims in this application, all restrictions on the availability to the public of the claimed isolated microbial strains listed in Table 2 will be irrevocably removed.

The isolated microbial strains identified herein were deposited on the indicated dates in accordance with the Budapest Treaty in the Agricultural Research Service Culture Collection, (NRRL), 1815 North University Street, Peoria, Ill., 61604, USA. Access to the deposits will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the deposited microbial strains will be irrevocably removed.

VIII. EXAMPLES

The following examples are included to demonstrate embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Isolation of Plant Growth-Promoting Microbes from *Medicago* Root Nodules

Naturally occurring *Medicago sativa* and *Medicago truncatula* plants were collected in winter and spring from open fields in Cal Poly Pomona and an open garden at the University of California, Los Angeles. Healthy-looking plants were chosen and their roots washed with sterile deionized water to remove soil. Young root nodules were screened, selecting the effective ones by their pink-red color and discarding those that appeared senescent. The nodules were surface-sterilized with commercial bleach (10% w/v), rinsed five times with sterile deionized water, and aseptically crushed. The macerate was inoculated on SA1 media (Trujillo et al., 2005) at 30° C. A total of 74 isolates were collected. The isolates are set forth in Table 3 below, along with the most closely related known species based on 16S rRNA sequence comparisons to the EZTaxon database.

TABLE 3

| Strain Designation | Closest Relative | Isolated from |
| --- | --- | --- |
| 2u118 | *Variovorax paradous* IAM 12373 | *M. sativa* |
| USAFOC | Not tested | *M. truncatula* |
| 1u117 | *B. aerophilus* 28K | *M. sativa* |
| 2u16 | *E. meliloti* LMG 6133 | *M. sativa* |
| 2u27 | E. meliloti LMG 6133 | *M. sativa* |
| 1u19 | *Ochrobactrum anthropic* ATCC 491888 | *M. sativa* |
| 4650D | *E. meliloti* LMG 6133 | *M. sativa* |
| 4677A | *E. meliloti* LMG 6133 | *M. sativa* |
| 1u115 | *E. meliloti* LMG 6133 | *M. sativa* |
| 2u15 | *E. meliloti* LMG 6133 | *M. sativa* |
| 2u111 | Not tested | *M. sativa* |
| 1u113 | *E. meliloti* LMG 6133 | *M. sativa* |
| 1u24b | Not tested | *M. sativa* |
| 4650F | *E. meliloti* LMG 6133 | *M. sativa* |
| USAF16 | *E. meliloti* LMG 6133 | *M. truncatula* |
| USAFOC8 | Not tested | *M. truncatula* |
| 1u10 | *E. meliloti* LMG 6133 | *M. sativa* |
| USAFOna16 | *B. subtilits* subsp. *subtilis* NCIB 3610 | *M. truncatula* |
| 2u210 | *Pseudonocardia carboxydivorans* Y8 | *M. sativa* |
| USAFOC17 | *Streptomyces naganishii* NBRC12892 | *M. truncatula* |
| 2u13 | *Ochrobactrum anthropi* ATCC 49188 | *M. sativa* |
| 2u114 | *Ochrobactrum anthropi* ATCC 49188 | *M. sativa* |
| USAF6 | *E. medicae* WSM419 | *M. truncatula* |
| USAFON2 | *Bacillus methylotropicus* KACC13105 | *M. truncatula* |
| 2u110 | *E. meliloti* LMG 6133 | *M. sativa* |
| 2u112 | Not tested | *M. sativa* |
| 1u118 | *E. arboris* LMG 14919 | *M. sativa* |
| 1u111 | *E. meliloti* LMG 6133 | *M. sativa* |
| utrum1' | *Ornithinibacillus contaminans* CC UG 53201 | *M. truncatula* |
| 2u18 | *E. meliloti* LMG 6133 | *M. sativa* |
| 1u116 | *E. meliloti* LMG 6133 | *M. sativa* |
| USAFON3 | Not tested | *M. truncatula* |
| USAFON1 | *E. arboris* LMG 14919 | *M. truncatula* |
| USAFOna6 | *Paenibacillus polymyxa* ATCC 842 | *M. truncatula* |
| USAF17 | *E. meliloti* LMG 6133 | *M. truncatula* |
| 1u112a | *R. smilacinae* PTYR-5 | *M. sativa* |
| USAF29PDA | Not tested | *M. truncatula* |
| 2u24 | *Ochrobactrum anthropic* ATCC 49188 | *M. sativa* |
| USAF1 | *E. arboris* LMG 14919 | *M. truncatula* |
| 1u114 | *E. meliloti* LMG 6133 | *M. sativa* |
| 2u17 | *E. meliloti* LMG 6133 | *M. sativa* |
| USAFOna4 | *Micromonospora auratinigra* TT1-11 | *M. truncatula* |
| UTRUM1 | *Micromonospora endolithica* DSM 44398 | *M. truncatula* |
| USAFOC20 | *Streptomyces sparsogenes* NBRC 13086 | *M. truncatula* |
| USAFOC6 | *Bacillus subtilis* subsp. *inaquosorum* KCtc 13429 | *M. truncatula* |
| PSB72 | Not tested | *M. sativa* |
| PSB33 | *Bacillus cereus* ATCC 14579 | *M. sativa* |
| PSB32 | *Bacillus cereus* ATCC 14579 | *M. sativa* |
| 2S(Ca)4 | Not tested | *M. sativa* |
| PSB36 | Not tested | *M. sativa* |
| 1SB12 | Not tested | *M. sativa* |
| PSB43' | *Bacillus altitudinis* 41KF2b | *M. sativa* |
| PSB43 | Not tested | *M. sativa* |
| 1SA(Ca)5 | *Bacilus safensis* FO-36b | *M. sativa* |
| 1SD10 | *B. atrophaeus* JCM 9070 | *M. sativa* |
| 2S(Ca)3 | *E. meliloti* LMG 6133 | *M. sativa* |
| PSCa3 | Not tested | *M. sativa* |
| PSCa18 | Not tested | *M. sativa* |

TABLE 3-continued

| Strain Designation | Closest Relative | Isolated from |
|---|---|---|
| PSCa25 | Not tested | *M. sativa* |
| 2S4 | Not tested | *M. sativa* |
| 15Sd13 | *B. lichenifomrmis* ATCC 14580 | *M. sativa* |
| PSB34 | *Bacillus safensis* 34 | *M. sativa* |
| 1SB7 | Not tested | *M. sativa* |
| PSB74 | Not tested | *M. sativa* |
| PSCA21 | *Bacillus subtilis* subsp. *inaquosorum* KCTC 13429 | *M. sativa* |
| PSB30 | Not tested | *M. sativa* |
| PSCA15 | *Bacillus dabaoshanensis* GSS04 | *M. sativa* |
| PSCA26 | Not tested | *M. sativa* |
| 1SD9 | Not tested | *M. sativa* |
| 1SB6 | *Bacillus muralis* LMG 20238 | *M. sativa* |
| 1SD11 | *Bacillus safensis* FO-36b | *M. sativa* |
| 1SB5 | *Bacillus simplex* NBRC 15720 | *M. sativa* |
| UTRUM2 | *Oceanobacillus caeni* S-11 | *M. truncatula* |
| PSB71 | *E. meliloti* LMG 6133 | *M. sativa* |

Phenotypic studies were performed on all of the isolates to characterize siderophore production, phosphate solubilization, cellulase activity, pectinase activity, caseinase activity, growth in nitrogen-free medium, halotolerance, and growth in media of different pH. CAS media was used to assay siderophore production, and PVK for phosphate solubilization as in Schwartz (2013). Cellulase activity was determined using CMC plates. Halotolerance was tested using SA1 media using several NaCl concentrations: 1%, 3%, and 5% (w/v). SA1 media was pH adjusted to 4.5, 5.5, 6, 8, and 9 to test for pH tolerance. The results of these assays are set forth in FIGS. 5A and 5B (PSB34 in FIG. 5B is also referred to herein as *Bacillus safensis* 34). The results in FIGS. 5A and 5B can be summarized as follows: 32% of the isolates solubilized phosphate, 19% produced siderophores, 75% were able to grow on nitrogen-free media, 29% of the isolates tested positive for cellulase activity, although a larger percentage, 82%, grew on a medium with cellulose as the sole-carbon source; 29% grew on pectin as a sole carbon source, and 33% grew on xylan as a sole carbon source; 26% were able to break down casein, showing they had proteinase activity; more than 89% of the isolates were able to tolerate pH 5.5-9, but only 25% grew at pH 4.5. Data for additional isolates are set forth below in Table 4.

ReadyMix (Sigma Aldrich) in a final volume of 25 µl per reaction, following the manufacturer's recommendations. PCR products were subjected to electrophoresis in 1% agarose gels containing ethidium bromide, using Tris-Acetate EDTA buffer. The amplified bands were excised and purified using Invitrogen PureLink™ Quick Gel Extraction Kit according to the manufacturer's instructions. Sequencing was performed by Macrogen, Inc. The isolates were identified using the EzTaxon server (Kim et al., 2012) on the basis of partial (~750 bp) 16S rRNA sequence data.

FIG. 1 shows the spread of *Micromonospora* species isolated from *Medicago truncatula* root nodules. The tree was inferred by using the Maximum Likelihood method based on the Kimura 2-parameter model (1000 boostrap replicates). The percentage of trees in which the associated taxa clustered together is shown next to the branches. The tree is drawn to scale, with branch lengths measured in the number of substitutions per site. *P. endophytica* was used as an outgroup.

Figure 2:
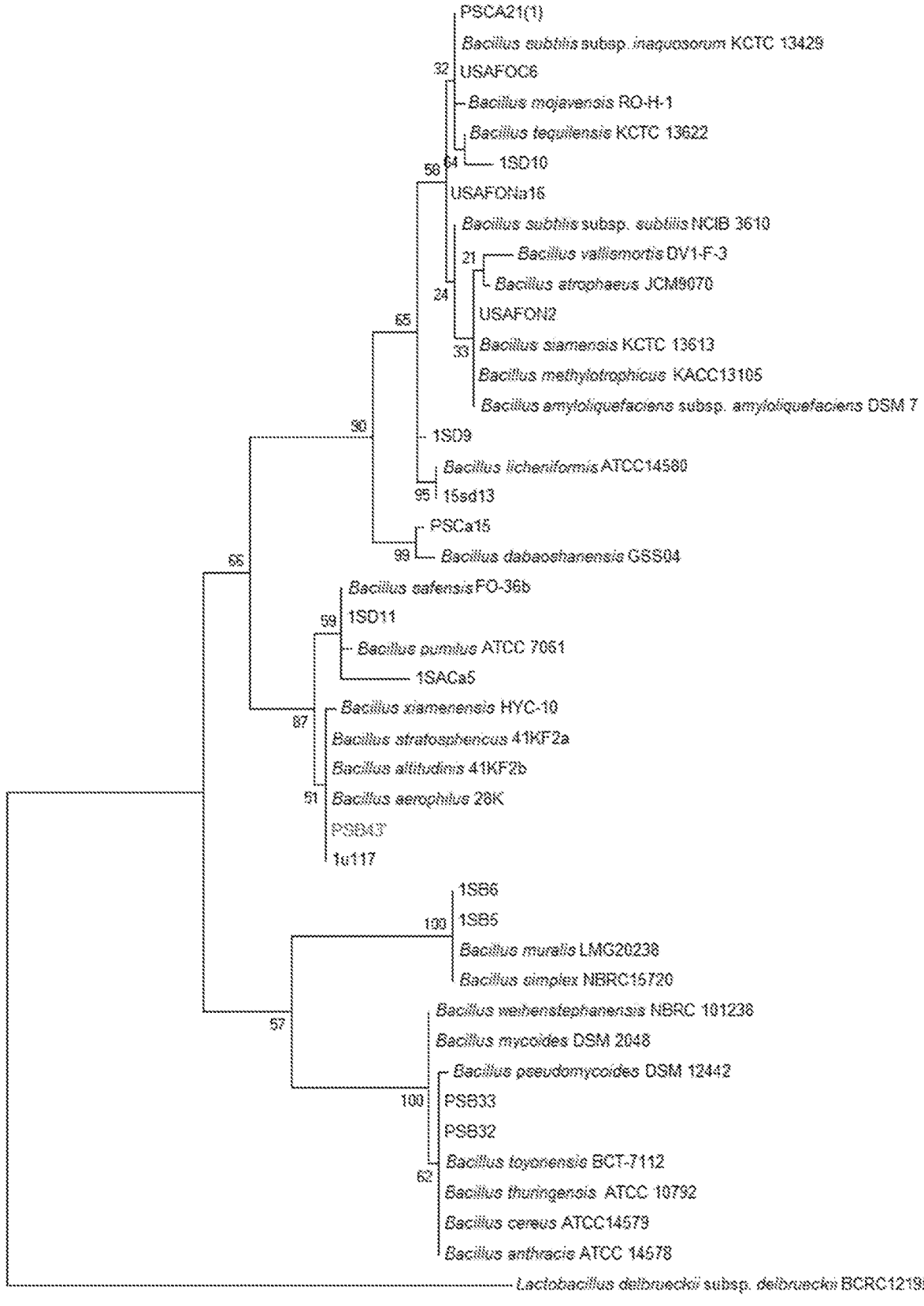
FIG. 2. Maximum likelihood phylogenetic tree of *Bacillus* bacteria isolated from *Medicago sativa* based on 16S rRNA gene sequences showing the relationship between the *Bacillus* isolates and the closest recognized *Bacillus* species. Bar, 0.020 substitutions per nucleotide position. Boostrap percentages (1000 replicates) above 50% are shown at nodes.

FIG. 2 shows the spread of *Bacillus* species isolated from *Medicago sativa* nodules. The tree was inferred by using the Maximum Likelihood method based on the Kimura 2-parameter model (1000 bootstrap replicates). The percentage of trees in which the associated taxa clustered together is shown next to the branches. The tree is drawn to scale, with branch lengths measured in the number of substitutions per site. *L. d. delbrueckii* was used an outgroup.

Example 3

In Planta Co-Inoculation of Isolated Bacteria with Em1021

Alfalfa seeds were sterilized with full-strength commercial bleach and germinated at 30° C. for three days in an incubator. The alfalfa plants were individually grown in plastic pots and incubated in a Conviron plant growth chamber in two trials. The substrate used was a 1:1 mix of Seramis® and vermiculite. For every trial, three treatment groups of potential PGPR strains were co-inoculated with *Ensifer meliloti* 1021 ("Em1021," an endophytic nitrogen-fixing symbiont of *Medicago*). Two positive control treatments were included: plants inoculated with Em1021, and plants co-inoculated with Em1021 and a known PGPR,

TABLE 4

| | C source CMC | C source Pectin | C source Xylan | N free medium | Casein | CMC | Sidero-phores production | Phosphate solubil-isation | pH 4.5 | pH 5.5 | pH 6 | pH 7 | pH 8 | pH 9 | NaCl 1% | NaCl 3% | NaCl 5% |
|---|---|---|---|---|---|---|---|---|---|---|---|---|---|---|---|---|---|
| *Bacillus* sp. 1SB5 | − | − | nd | − | nd | + | − | + | − | + | + | + | + | + | nd | nd | nd |
| *Oceanobacillus* sp. UTRUM 2 | + | − | − | − | + | − | − | − | − | − | − | + | + | + | + | + | + |
| *Bacillus* sp. 1SD11 | − | − | nd | − | nd | + | − | + | + | + | + | + | + | + | nd | nd | nd |

Example 2

16S rRNA Analysis of Isolates from *Medicago* Root Nodules

DNA was extracted from cell cultures using the REDExtract-N-Amp™ PCR ReadyMix (Sigma Aldrich) following the manufacturer protocol. 16S PCR amplifications for each strain were performed using fD1 and rD1 primers and the PCR mixture included in the REDExtract-N-Amp™ PCR

Figure 3A:
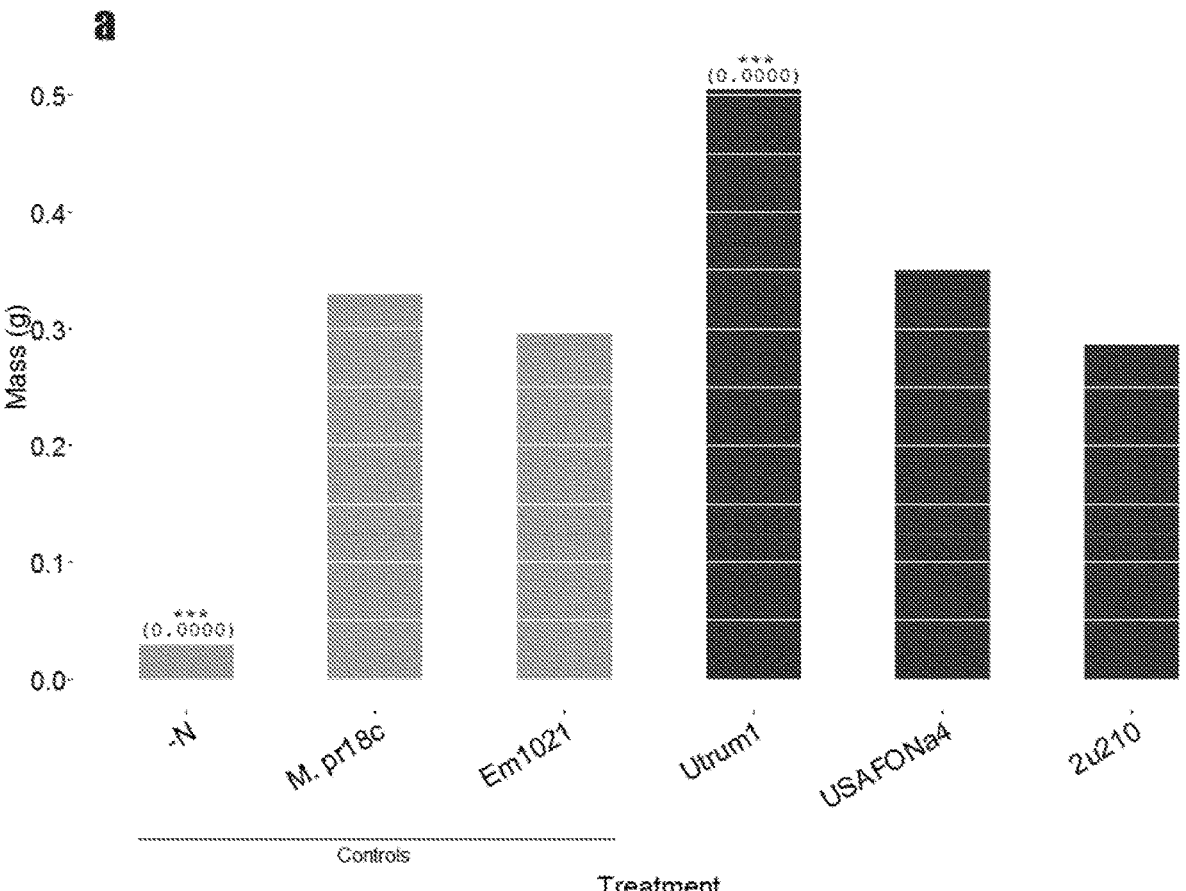
FIGS. 3A-3F. *Micromonospora* strains enhance the symbiosis between alfalfa and *Ensifer meliloti* 1021. Comparison of measures of the indicated physical parameters after the various inoculation treatments (n=10). ANOVA and posthoc LSD analysis were performed for comparing the co-inoculation treatments of the indicated strains with Em1021 (bars labeled Utrum 1, USAFONa4, and 2u210) and Em1021 single inoculant (bars labeled Em1021). Statistical significance indicated by an asterisk, with p-values in parentheses. Significance (p-value) codes: ***<0.001; **<0.01; '*'<0.05-N, nitrogen-free control treatment; M. pr18c, previously described PGPM; Em1021, *Ensifer meliloti* 1021.
Figure 3B:
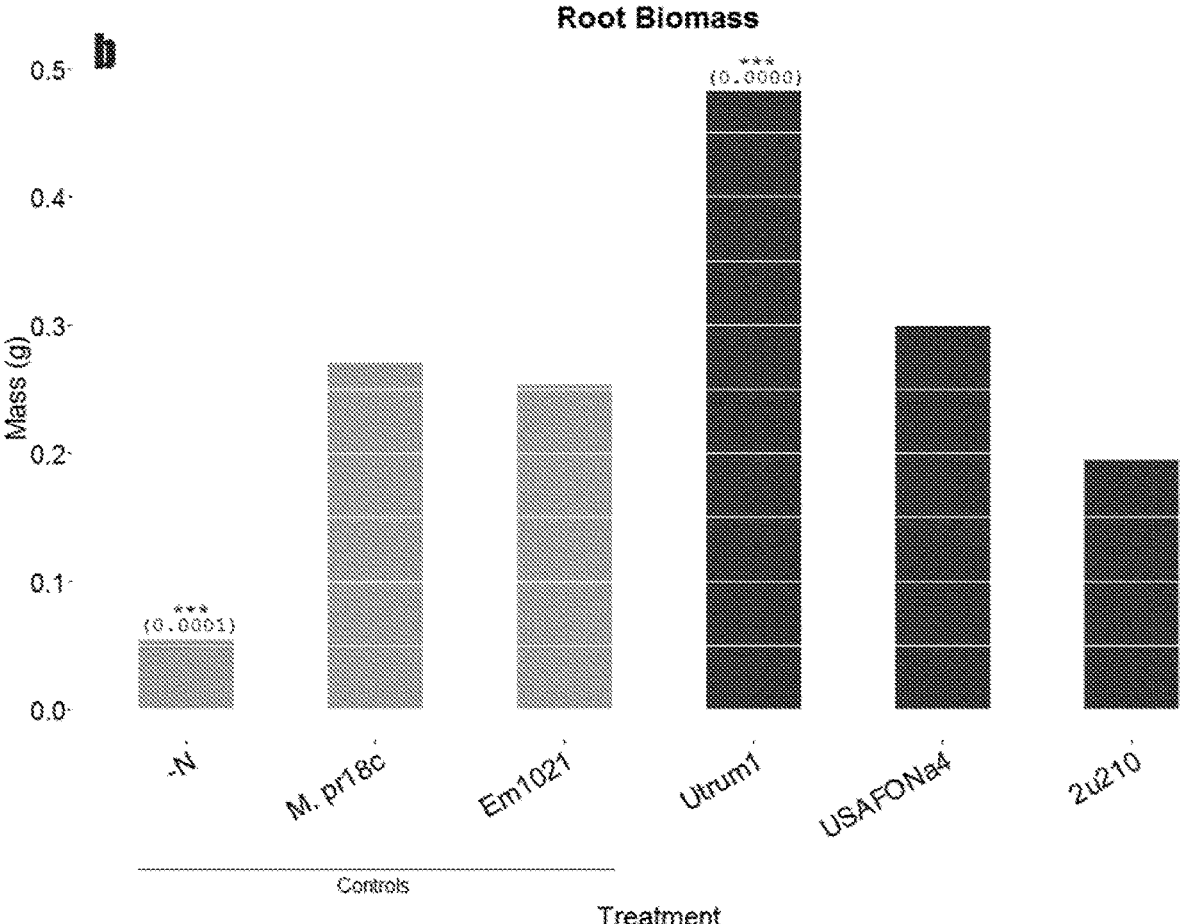
Figure 3C:
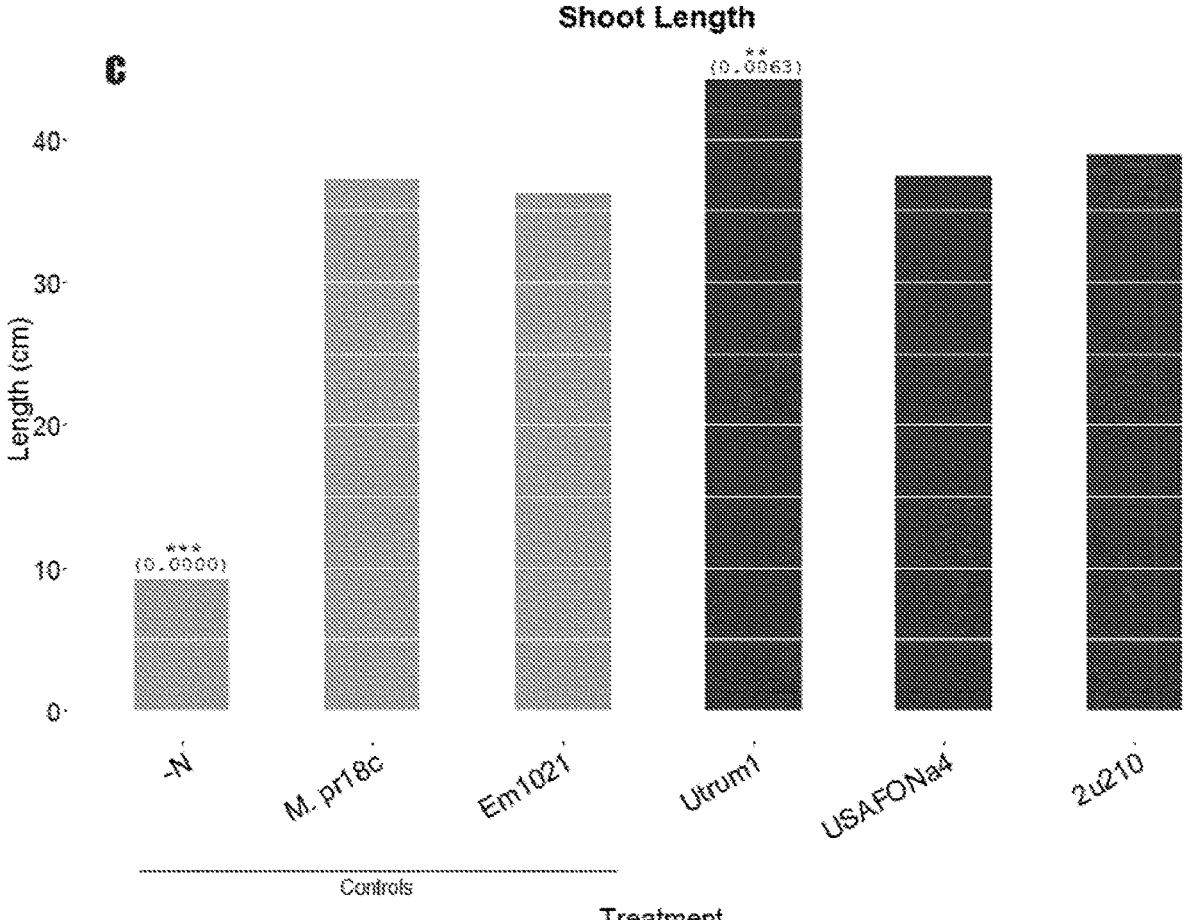
Figure 3D:
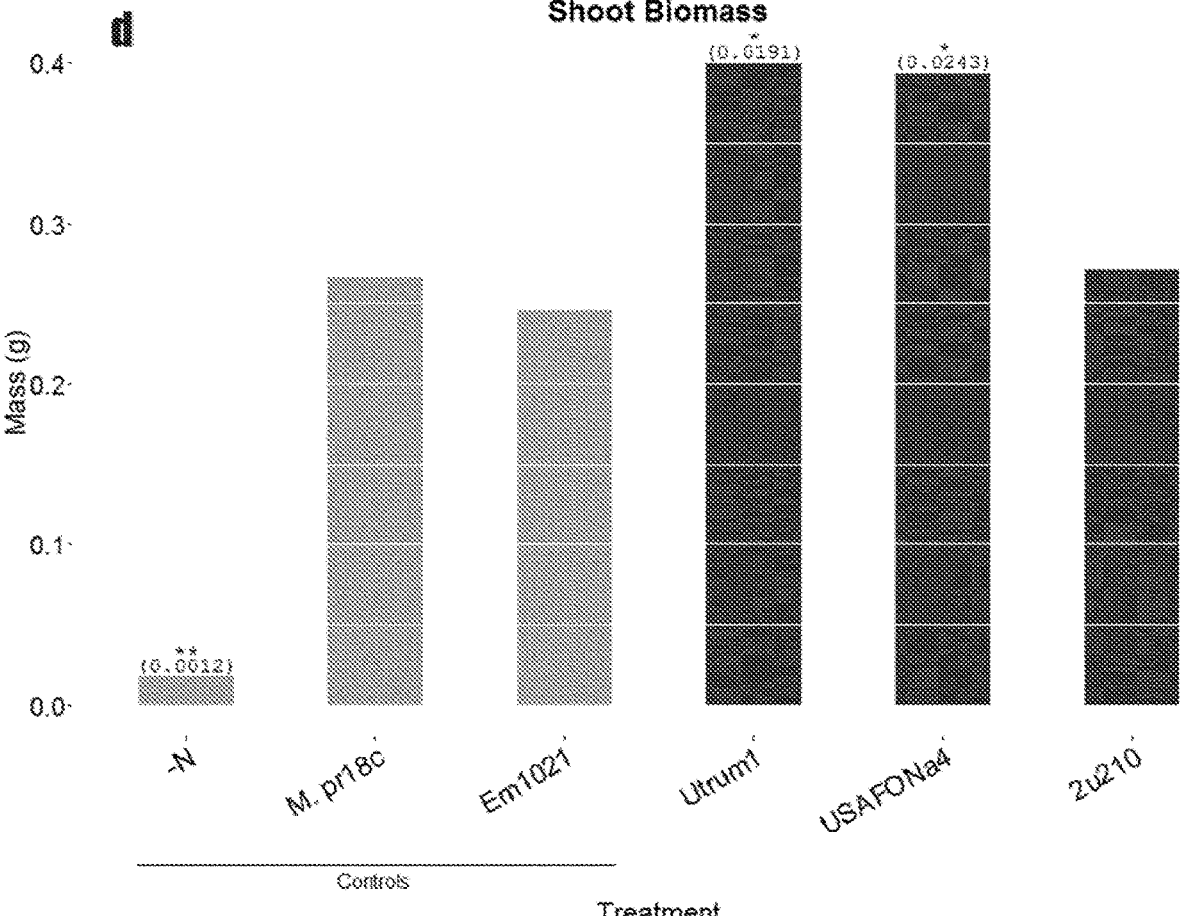
Figure 3E:
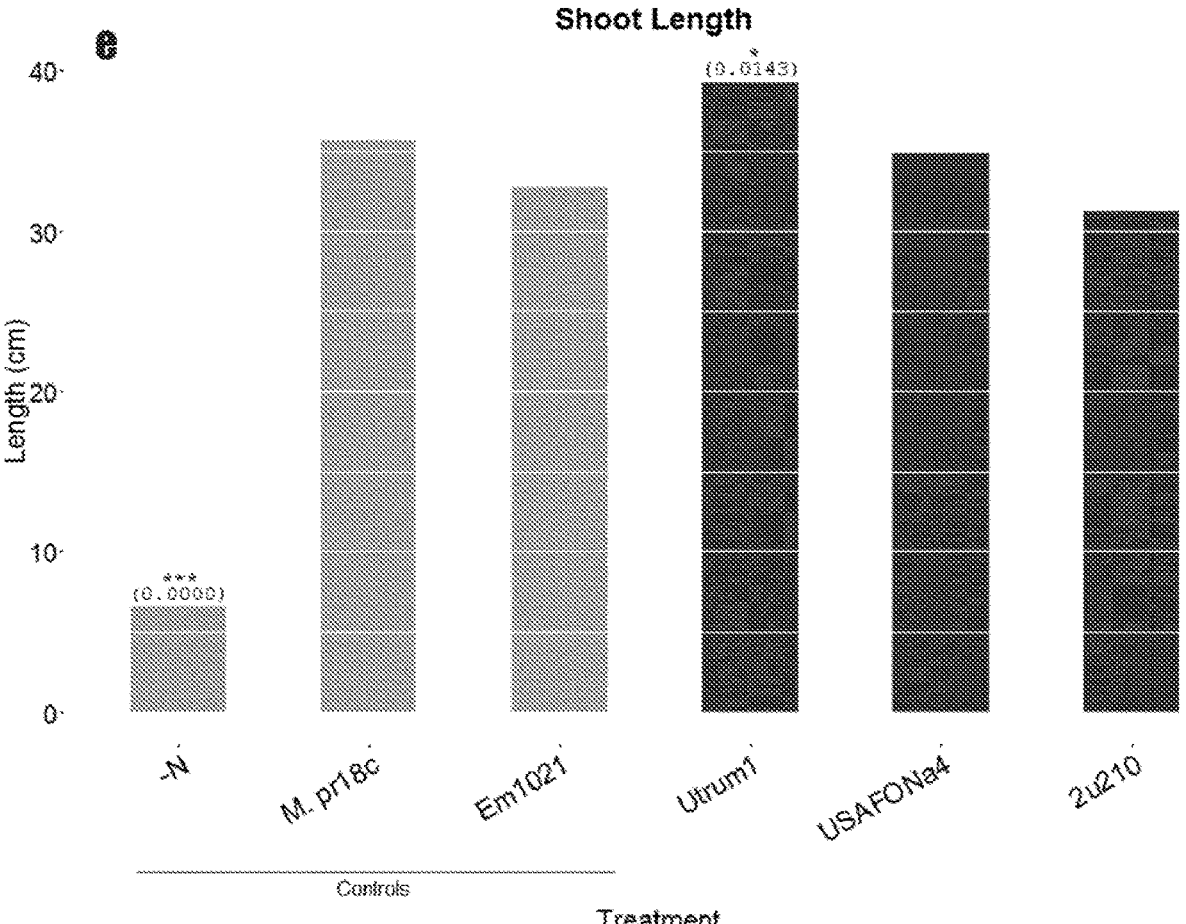
Figure 3F:
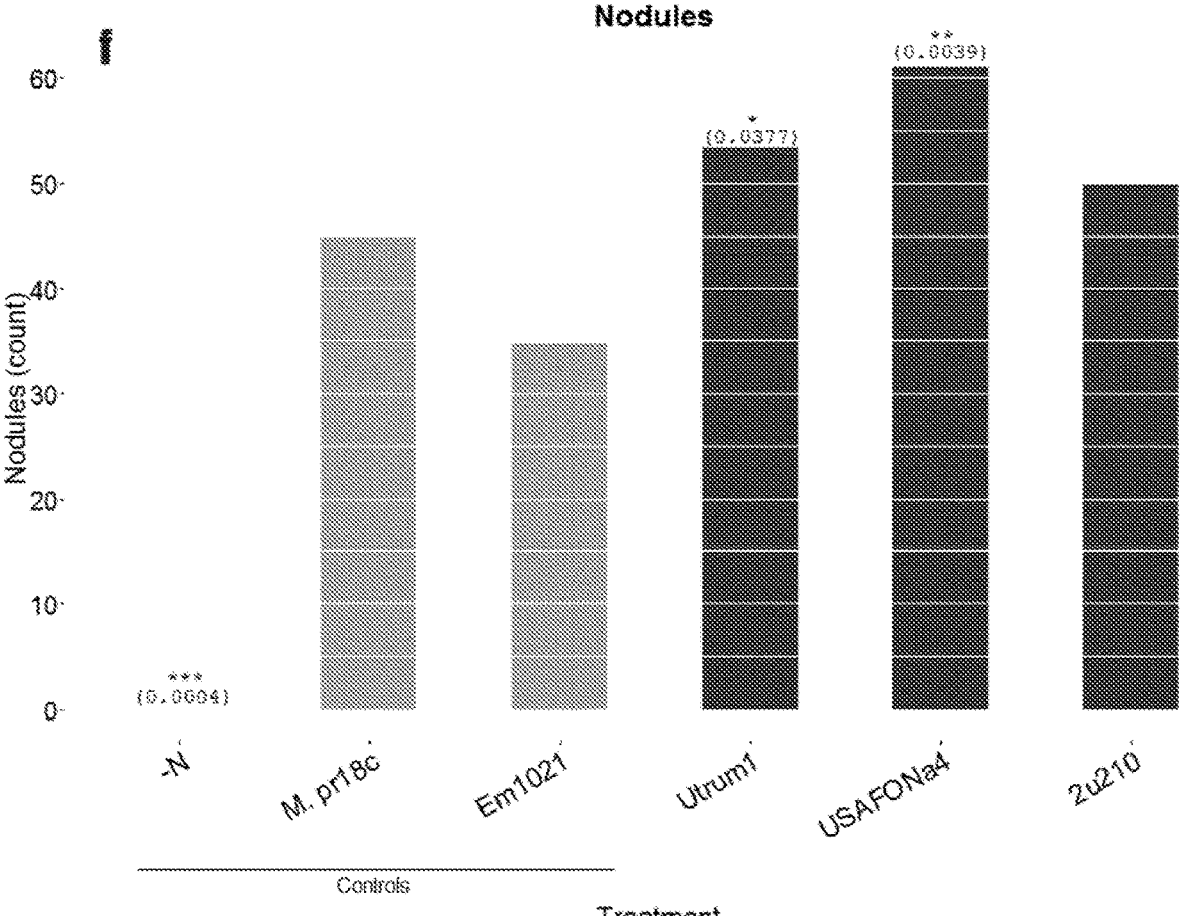

*Micromonospora* pr18 (Martinez-Hidalgo 2014). Eight to ten replicates were used for controls, while ten replicates were used per experimental treatment. The strains tested in trial one were: 2u210, USAFONa4, and UTRUM1 (FIGS. 3A-3C). A second trial with these same strains was performed (FIGS. 3D-3F). An experiment was also performed in the same way with strains 1SA (CA) 5 (*Bacillus*), PSB43 (*Bacillus*), and USAFOC20 (*Streptomyces*). For inoculation, colonies of each isolate were suspended in sterile deionized water and adjusted to a McFarland standard number six and one mL of solution pipetted at the base of the alfalfa seedling into the Seramis-vermiculite mix. Root and shoot biomass were measured dry. Root and shoot length were recorded by measuring the primary root and shoot. Statistical analysis of data, using ANOVA and posthoc LSD analysis, was conducted in IBM SPSS 23 and RStudio 0.99.

FIGS. 3A-3F show that Utrum1 and USAFONa4 significantly enhance the symbiosis between alfalfa and Em1021. In the first trial, co-inoculation with Utrum1 significantly increased shoot biomass, root biomass, and shoot length compared to inoculation with Em1021 alone (FIGS. 3A-3C). In the second trial, co-inoculation with Utrum1 significantly increased shoot biomass, shooth length, and number of nodules compared to inoculation with Em1021 alone, and USAFONa4 significantly increased shoot biomass and number of nodules compared to inoculation with Em1021 alone (FIGS. 3D-3F).

Figure 4A:
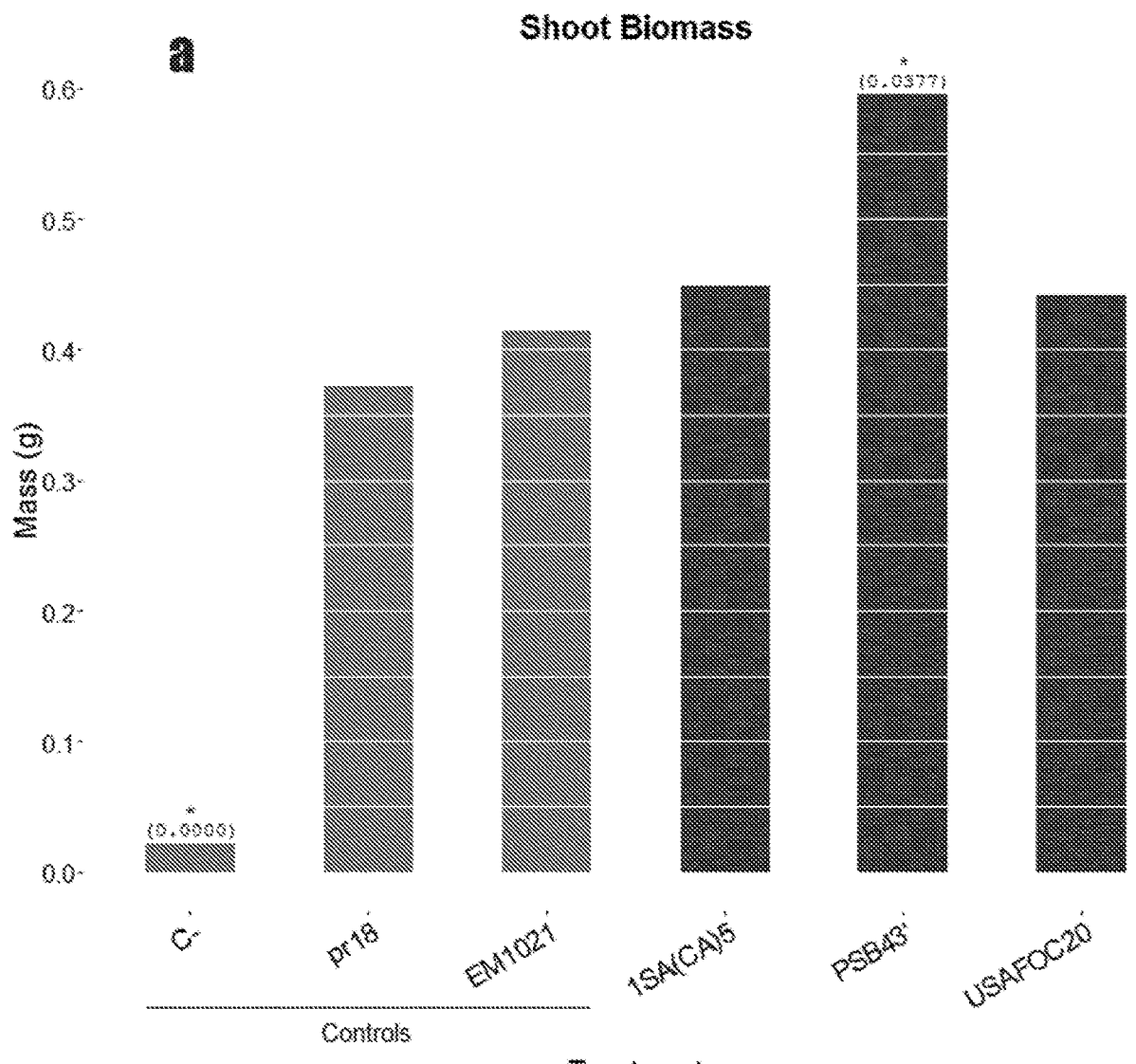
FIGS. 4A-4C. Co-inoculation with *Bacillus* PSB43' increases shoot biomass (dry), enhances nodulation, and increases shoot length in alfalfa. Comparison of measures of the indicated physical parameters after various inoculation treatments (n=10). ANOVA and posthoc LSD analysis were performed for comparing between co-inoculation treatments of the indicated strains with Em1021 (bars labeled 1SA (CA) 5, PSB43', and USAFOC20) and the Em1021 single inoculant (bar labeled Em1021). Statistical significance indicated by an asterisk, with p value in parentheses.
Figure 4B:
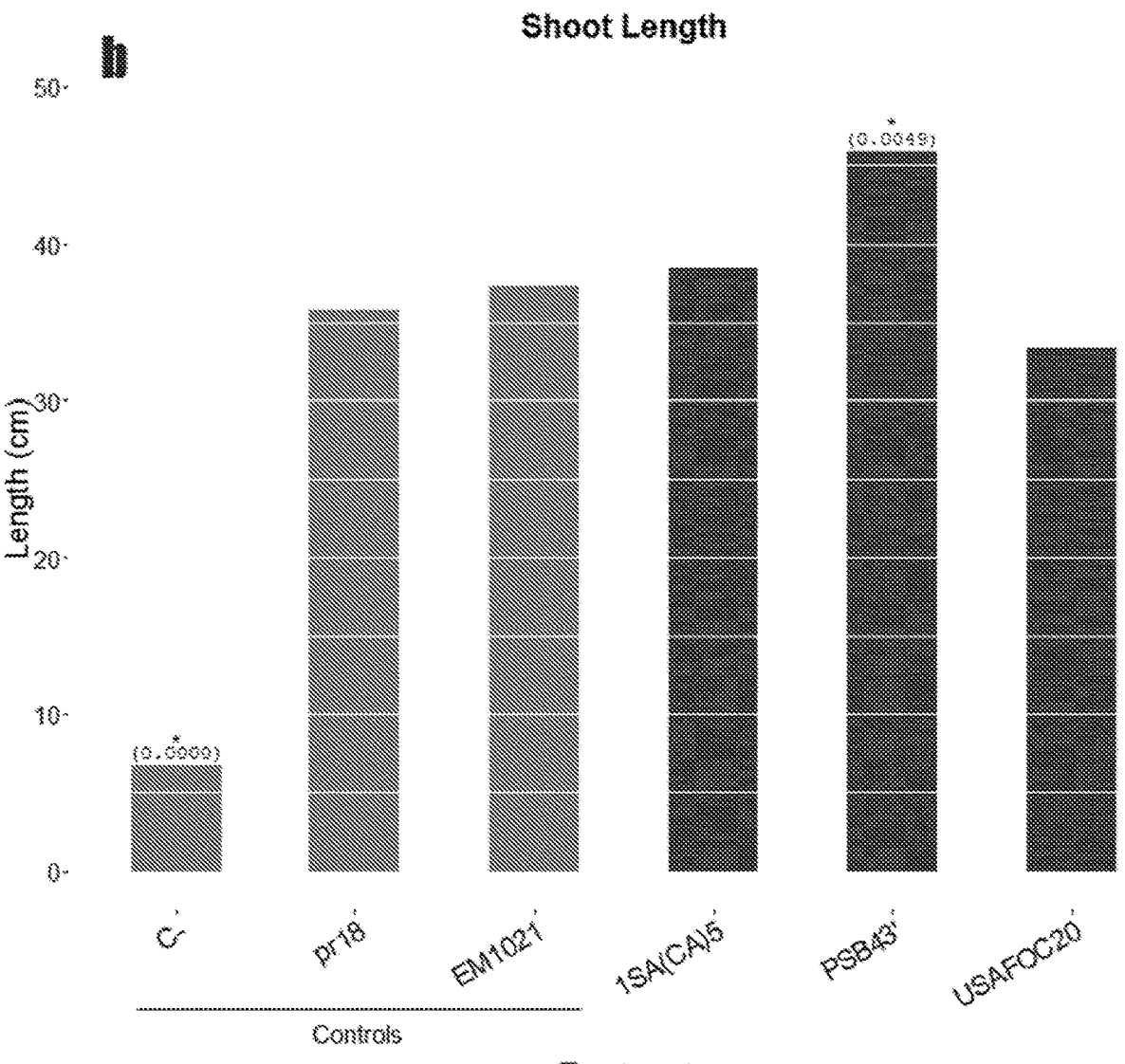
Figure 4C:
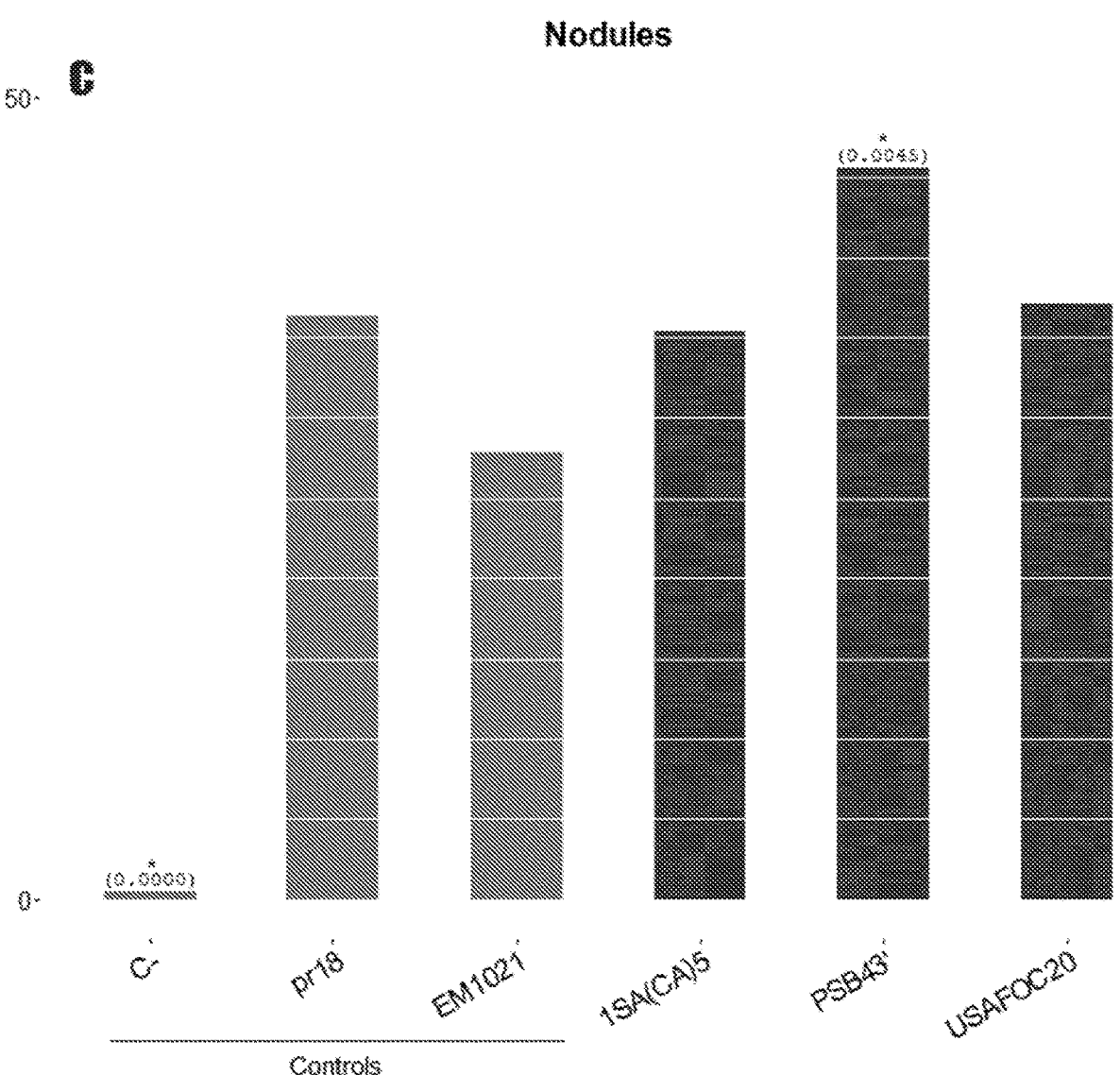

FIGS. 4A-4C show that PSB43' significantly enhances the symbiosis between alfalfa and Em1021. Co-inoculation with PSB43' significantly increased shoot biomass, shoot length, and number of nodules compared to inoculation with Em1021 alone.

Example 4

Isolation of Additional Plant Growth-Promoting Microbes

Additional plant growth-promoting bacteria were isolated from various soil samples. Isolation from soil was done by placing soil samples in sterile PBS with glass beads and shaking vigorously, both by hand and on a rotary shaker. After briefly allowing the resulting suspension to settle, a portion of the suspension was taken and serially diluted. Dilutions were plated onto rich, non-selective medium (LB) and on selective media that can be diagnostic for nitrogen fixation and then incubated in the dark at 25° C. Genomic DNA was extracted from bacteria from individual colonies, rRNA genes were amplified by PCR, and the PCR products were sequenced. Sequences were compared to several databases and the most closely related species were identified. Table 5 lists bacteria isolated, along with the source of the strain.

TABLE 5

| Strain Designation | Closest Relative | Isolated from |
|---|---|---|
| *Paenibacillus pabuli* 151 | *Paenibacillus pabuli* | soil from the Negev desert |
| *Dietzia cinnamea* 55 | *Dietzia cinnamea* | soil from the Negev desert |
| *Lysinobacillus sphaericus* 47 | *Lysinobacillus sphaericus* | soil from the Negev desert |
| *Paenibacillus MBEV37* B17 | *Paenibacillus MBEV37* | soil from Botswana |
| *Exiguobacterium alkaliphilum* 20 | *Exiguobacterium alkaliphilum* | soil |
| *Paenibacillus tundrae* 47' | *Paenibacillus tundrae* | soil |
| *Bacillus simplex* 237 | *Bacillus simplex* | soil from the Negev desert |

In experiments to test for the ability to promote plant growth, each of the strains listed in Table 5 was shown to promote at least one aspect of plant growth.

Example 5

Identification of Abiotic Stress Tolerant Strain 55

Various bacteria samples were collected from the Negev Desert, Israel from various sites and pooled to form a composite sample. This mixture was immediately transported to a laboratory for isolation and identification of cultivatable rhizosphere bacteria.

Preliminary screening included the assessment of bacterial strains for their ability to tolerate abiotic stresses by streaking them on Luria-Bertani (LB) agar plates supplemented with NaCl (2, 4, and 6% w/v) to test for salinity stress; PEG (polyethylene glycol; aver. mol. wt. 3,350 at 30, 45, and 60%) for drought stress, and pH (4 and 9) for pH stress. Media plates that contained neither salt nor PEG at pH 7.0 served as controls. The growth of strains at high temperature was also assessed by placing a set of streaked plates in a Fisher Scientific Incubator (Model 655D) adjusted to 37° C. For all the experimental sets, plates incubated at 30° C. served as the control and bacterial growth was observed over a period of 10 days.

The abiotic stress tolerance of a selected strain was re-assessed in shake-flask conditions by growing the individual bacterial cultures under control (0% NaCl, pH 7, 300C), saline (2, 4 and 6% w/v NaCl, pH 7, 30° C.), and drought (0% NaCl, pH 7, 30, 45, and 60% PEG 3350, 30° C.) conditions in 150 ml Erlenmeyer flasks containing 50 ml LB, with an initial inoculum of about 107 CFU/ml. The flasks were incubated in a New Brunswick Scientific Co. (Edison, NJ, USA) Series 25 incubator shaker at 180 rpm. Viable cells (CFU/ml) were counted at various time intervals for up to 15 days by serial dilution plating on LB agar plates in triplicate.

Physiological characterization of the selected strain was performed for various plant growth promotion abilities including the production of cellulase, pectinase, xylanase and protease was conducted following standard protocols. Siderophore production and phosphate solubilization activity were determined on CAS agar and PVK plates respectively.

For phylogenetic analysis, bacteria were suspended from a single colony grown on LB agar plates into 20 μL of sterile distilled water (SDW). The gene for 16S rRNA was amplified by PCR using the forward primer fD1 and the reverse primer rD1 (Weisberg et al, 1991). Amplification was performed in a total volume of 25 μL containing 14.9 μL SDW, 1 μL of bacterial lysate sample, 2.5 μL of 10×Taq Buffer (MgCl2), 0.5 μL fD1 and rD1 (10 μM), 0.5 μL dNTPs (10 mM), 5 μl Q solution and 0.125 μL Taq DNA polymerase. Amplified 16S rDNA products were visualized with ethidium bromide both in the gel and in the gel electrophoresis running buffer and purified from a 0.8% low-melting point agarose gel (100 V, 400 mA, 1 h). The gel extraction was performed with the Invitrogen Quick Gel Extraction Kit according to the manufacturer's directions. The samples were then sent to Laragen Inc. for further processing and sequencing. The nucleotide sequences were compared against nucleotide databases using the NCBI BLASTn and EzTaxon server 2.1 programs to identify the closest known taxa. The 16S rRNA gene along with their closest homology sequences were aligned using multiple sequence alignment program CLUSTAL W algorithm implemented in MEGA 6 software by using default parameters. The phylogenetic tree was constructed by neighbor-joining (NJ) method using the MEGA 6 program and evolutionary distances were computed with the help of Kimura's 2 parameter models. The bootstrap analysis with 1000 replications using p-distance model was performed based on the original dataset to estimate the confidence of a particular clade.

Figure 6:
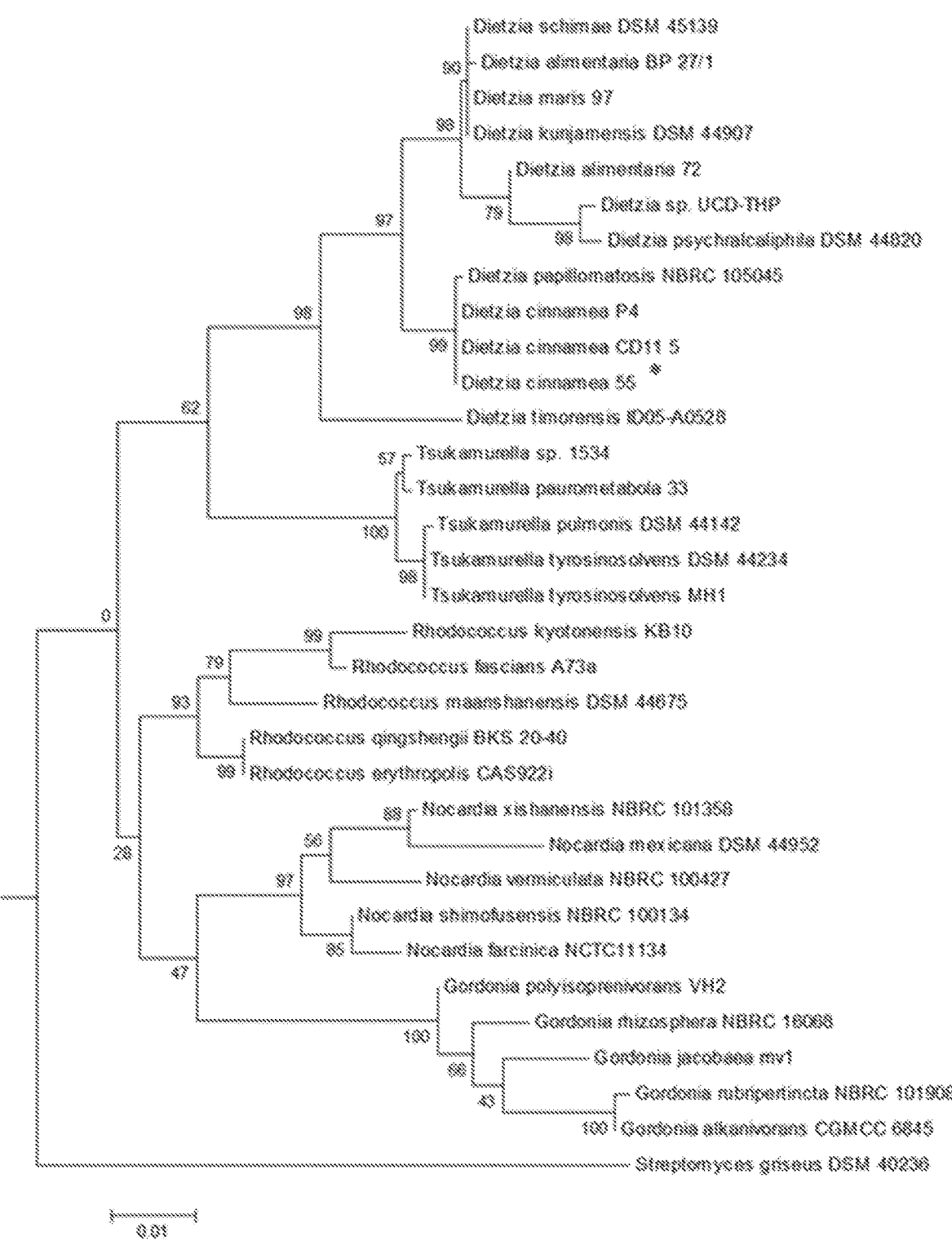
FIG. 6. Phylogenetic tree based on the 16S rRNA gene showing the relationship between *Dietzia Cinnamea* 55. Bar, 0.01 substitutions per nucleotide position.

The in vitro experiments conducted on plates demonstrated that strain 55 is an efficient salt-, pH-, and drought-tolerant bacterial species compared to the 40 other bacterial isolates tested. Molecular characterization based on 16S rDNA sequence analysis indicated that strain 55 has the closest phylogenetic relationship to *Dietzia cinnamea* with 99% homology (FIG. 6). A growth curve of strain 55 in the presence of 2%, 4%, and 6% NaCl was monitored at 30° C. to up to 15 days. Strain 55 survived mild salt stress conditions with a final CFU of ~107-8 CFU/ml on day 15. However, a reduced CFU (~105-6 CFU/ml) was observed in 6% NaCl. A similar trend was recorded in 30%, 45%, and 60% PEG over a period of 15 days, where strain 55 exhibited a CFU of 105-6 CFU/ml for all three concentrations of PEG tested. Also, the strain 55 was found to be sensitive to 37° C. temperature as the plates incubated at 37° C. demonstrated no growth in comparison to the control plates incubated at 30° C. where strain 55 grew well.

Among the plant-growth promotion attributes that influence endophytic entry into the plant as well as antagonistic behavior against other microbes, strain 55 tested positive for cellulase, xylanase, protease, pectinase, and amylase. Biochemical assays for the presence of siderophores and the ability to solubilize phosphate demonstrated that strain 55 performed both functions.

Example 6

Promotion of Corn Growth by *Dietzia cinnamea* 55
Pot Trials

Seeds of *Zea mays* L. (Corn Golden Bantam), obtained from Baker Creek Heirloom Seed Company, Mansfield, MO, United States, were surface-sterilized by immersing them in 70% ethanol for 1 min, followed by three rinses with SDW. For the treatments, the seeds were bacterized for 3 h by imbibing them in a bacterial suspension, which had been grown for 48 h to contain approximately 109 CFU/ml. Seeds imbibed in LB medium served as the control. The treatments consisted of control and *Dietzia cinnamea* 55-treated plants grown in sterile Sungro Potting Mix containing mainly Canadian sphagnum peat moss along with a small fraction of coarse perlite and dolomitic limestone. Eight replicates of each treatment, with four plants in each pot, were maintained. Soil moisture was maintained to approximately 20% with water. Plants in all the treatments were grown in parallel and harvested at the same time after 45 days of sowing. Measurements on morphological parameters, namely shoot length and root length were recorded at the time of harvesting. Plant dry weight measurements were made after drying the plants in a 60° C. oven. The trial was repeated three times and the data were generated from the pooling of all the trials. The data are presented as mean±standard deviation (SD). The statistical analysis was performed using GraphPad Prism software version 5.01 (GraphPad Software, San Diego, CA, USA).

Table 6 below shows the results of the measurements of shoot length, root length, and dry plant biomass for the plants grown from the *Dietzia cinnamea* 55-bacterized seeds and control seeds.

TABLE 6

| Treatments | Shoot length (inches) | Root length (inches) | Dry Plant Biomass (g) |
|---|---|---|---|
| Control | 32.08 ± 4.62 | 16.63 ± 3.99 | 10.09 ± 2.93 |
| *Dietzia cinnamea* 55 | 41.94 ± 5.54 | 19.34 ± 2.49 | 17.70 ± 4.95 |

Microplot Studies

Untreated control *Zea mays* L. seeds and *Dietzia cinnamea* 55-treated seeds were sown in a microplot (2 m×2 m) in an outside garden in four rows, two for each treatment. Seeds were treated as described above. Each row had 12 plants, with an intra- and inter-row spacing of about 20 and 60 cm, respectively. Harvesting was carried out after 120 days of sowing, followed by the recording of the plant data. The experiment was repeated three times, and the data presented results from the pooling of all trials. The data are presented as mean±standard deviation (SD). The statistical analysis was performed using GraphPad Prism software version 5.01 (GraphPad Software, San Diego, CA, USA).

Table 7 below shows the results of the measurements of shoot length and dry plant biomass for the plants grown from the *Dietzia cinnamea* 55-bacterized seeds and control seeds.

TABLE 7

| Treatments | Shoot length (inches) | Dry Plant Biomass (g) |
|---|---|---|
| Control | 33.71 ± 10.01 | 29.66 ± 5.10 |
| *Dietzia cinnamea* 55 | 47.19 ± 6.21 | 40.37 ± 8.72 |

Figure 7:
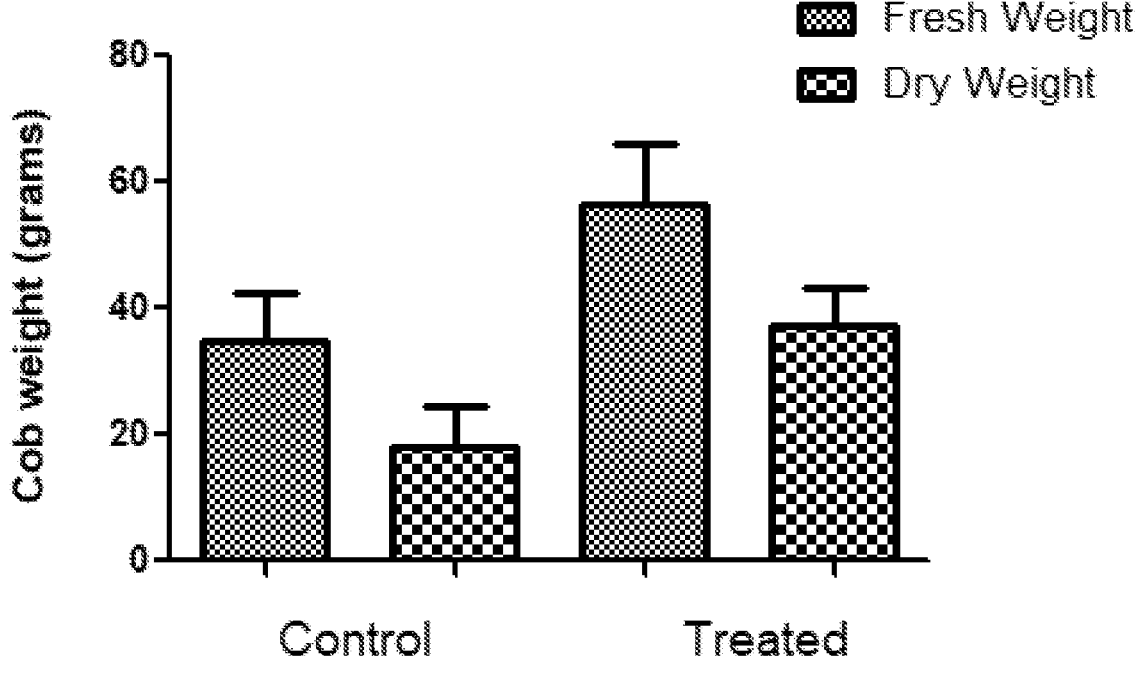
FIG. 7. Promotion of plant growth by *Dietzia cinnamea* 55. Fresh and dry weight of cobs are shown for corn plants grown from seeds contacted with *Dietzia cinnamea* 55 culture ("Treated") and from control, untreated seeds.

The results for cob yield are shown in Table 8 below and in FIG. 7.

TABLE 8

| Treatments | Fresh wt. of 10 cobs (g) | Dry wt. of 10 cobs (g) |
|---|---|---|
| Control | 34.8 ± 7.63 | 17.9 ± 6.54 |
| *Dietzia cinnamea* 55 | 56.5 ± 9.73 | 37.3 ± 5.77 |

The results of these experiments show that treatment of corn seeds with *Dietzia cinnamea* 55 promotes plant growth by multiple measures of plant growth.

Example 6

Virulence Analysis of *Dietzia cinnamea* 55 with *C. elegans*

The activity of *C. elegans* fed with strain 55 under slow-killing conditions was assayed. The test bacteria were spread on two nematode growth media (NGM) plates and incubated at 30° C. for 24 h. Each plate was seeded with a known number of nematodes from the original control plate (*Escherichia coli* OP50), which was determined using a Zeiss microscope at 10× magnification (Carl Zeiss, Oberkochen, Germany). This number served as a zero-h reading. After counting, the plates were incubated at 25° C. and scored for nematode death every 24 h for 5 days. The strain *E. coli* OP50 served as a control for estimating the natural death rate of the nematodes and *Pseudomonas aeruginosa* PA14 was the positive control for pathogenicity. The experiment was conducted three times with two replicates of the bacterial strain. A pathogenic score (PS 1, 2, or 3) was given based on the number of disease criteria observed. A strain was considered non-pathogenic when no symptoms of disease were observed (PS 0). Additionally, the influence of the bacteria on movement and propagation of the nematodes was monitored for 120 h. The data are presented as mean±standard deviation (SD). The statistical analysis was performed using GraphPad Prism software version 5.01 (GraphPad Software, San Diego, CA, USA).

Figure 8:
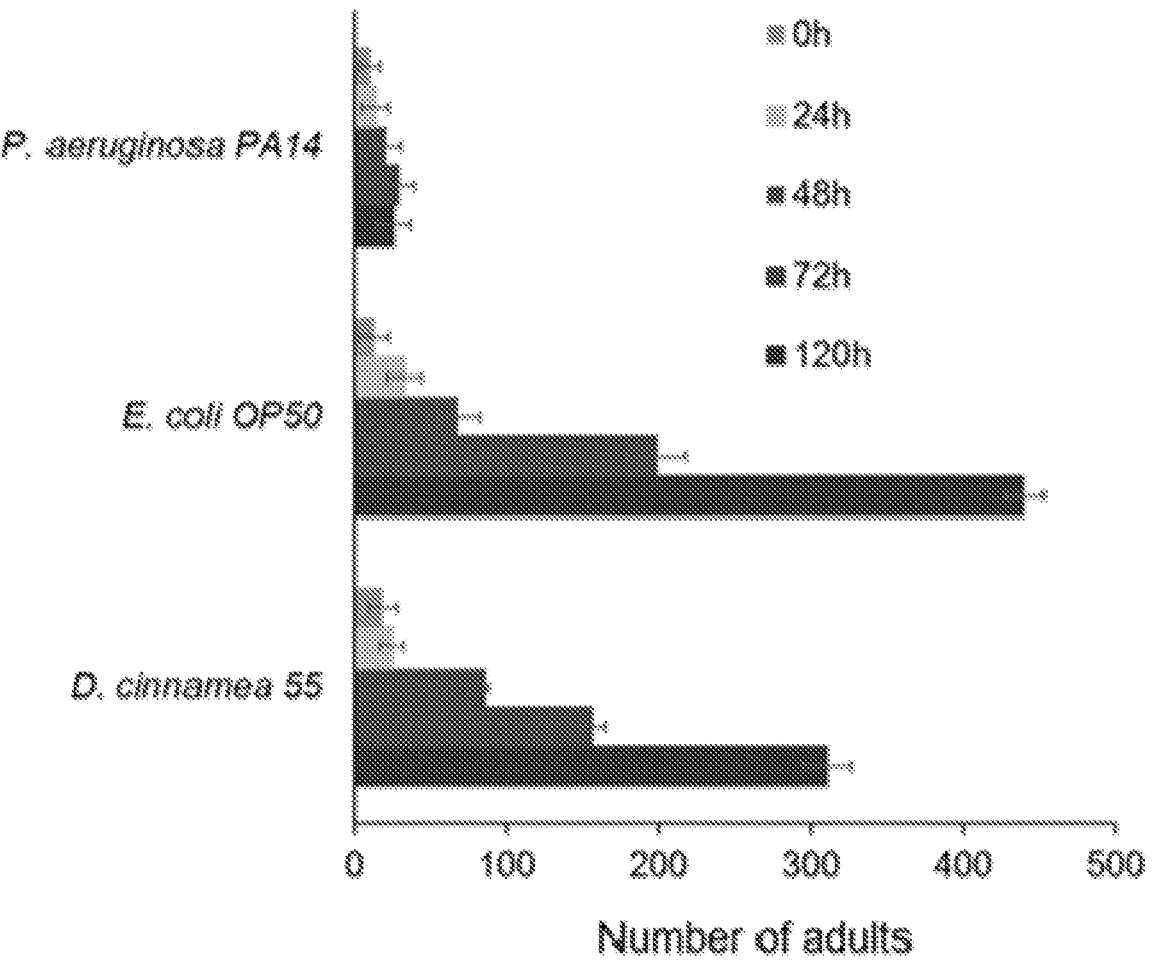
FIG. 8. Pathogenicity test of *Dietzia cinnamea* 55 using *C. elegans*. Live nematode counts at each time point are shown.

On NGM, *C. elegans* exposed to PA14 were motile, but avoided the bacteria, which remained unconsumed by the nematodes, which led to their death in contrast to their normal food source, *E. coli* OP50, which had no effect on worm viability. The test strain *D. cinnamea* 55 did not show any inhibitory effect on the motility and growth of worms. FIG. 8 and Table 9 below show the results of the virulence analysis.

TABLE 9

| Strains | PS | Motility | Accumu-lation in Batches | Acoidance of bacterial lawn | Digestion of bacterial lawn |
|---|---|---|---|---|---|
| *Pseudomonas aeruginosa* PA14 | 3 | Very slow | — | Around edge | |
| *E. coli* OP50 | 0 | Fast | By 72 hr | | By 48 hr |
| *D. cinnamea* 55 | 0 | Fast | By 72 hr | | By 72 hr |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All references, cited literature articles, patent publications, and sequences associated with any recited GenBank accession numbers are specifically incorporated herein by reference in their entirety for all purposes.

The invention claimed is:

1. A method of increasing one or more plant growth characteristics in a plant, comprising: providing to the plant an effective amount of one or more of the following plant growth-promoting microbial isolates: *Dietzia cinnamea* 55 (NRRL Accession No. B-67422), *Bacillus* PSB43' (NRRL Accession No. B-67416), *Micromonospora* UTRUM1 (NRRL Accession No. B-67418), *Paenibacillus pabuli* 151 (NRRL Accession No. B-67417), *Lysinobacillus sphaericus* 47 (NRRL Accession No. B-67423), *Paenibacillus* MBEV37 B17 (Accession No. B-67419), *Exiguobacterium alkaliphilum* 20 (NRRL Accession No. B-67425), and *Bacillus safensis* 34 (NRRL Accession No. B-67620).

2. The method of claim 1, wherein the plant is provided two or more of the plant growth-promoting microbial isolates.

3. The method of claim 1, wherein the one or more plant growth-promoting microbial isolates comprises *Bacillus* PSB43'.

4. The method of claim 1, wherein the one or more plant growth-promoting microbial isolates comprises *Micromonospora* UTRUM1.

5. The method of claim 1, wherein the plant is further provided an effective amount of one or more rhizobial bacterial strains.

6. The method of claim 1, wherein providing to the plant an effective amount of the one or more plant growth-promoting microbial isolates comprises contacting seed of the plant with the one or more plant growth-promoting microbial isolates.

7. The method of claim 1, wherein providing to the plant an effective amount of the one or more plant growth-promoting microbial isolates comprises adding the one or more plant growth-promoting microbial isolates to soil in which the plant is growing or will grow.

8. The method of claim 1, wherein providing to the plant an effective amount of the one or more plant growth-promoting microbial isolates comprises contacting a part of the plant with the one or more plant growth-promoting microbial isolates.

9. The method of claim 8, wherein the part comprises the plant roots.

10. The method of claim 8, wherein the part comprises the plant rhizosphere.

11. The method of claim 1, wherein the plant is a dicotyledon, a crop plant, or a legume.

12. The method of claim 1, wherein the plant is corn.

13. The method of claim 1, wherein the one or more plant growth-promoting microbial isolates comprises *Dietzia cinnamea* 55.

14. The method of claim 1, wherein the one or more plant-growth promoting microbial isolates have one or more of the following characteristics: nitrogen fixation, siderophore production, iron chelation, phosphate solubilization, chitinase production, cellulase production, pectinase production, xylanase production, growth at pH 4.5, growth at pH 5.5, and growth in 5% NaCl.

15. The method of claim 1, wherein the one or more plant growth characteristics comprise one or more of the following: plant biomass, plant growth rate, plant yield, shoot length, shoot biomass, fresh cob weight, dry cob weight, root biomass, nodulation, nitrogen utilization, nutrient utilization, salt tolerance, resistance to one or more pathogens, resistance to fungal growth, growth under arid conditions, growth under arid soil conditions, growth under low pH conditions, growth under low pH soil conditions, growth under high pH conditions, growth under high pH soil conditions, growth under low temperature conditions, growth under low temperature soil conditions, growth under high temperature conditions, and growth under high temperature soil conditions.

16. The method of claim 10, wherein the plant rhizosphere comprises one or more of roots, root nodules, root caps, root exudate, rhizosphere-associated microorganisms, and rhizosphere-associated soil.

17. The method of claim 13, wherein the plant is corn.

18. The method of claim 13, wherein the plant is corn and wherein the providing to the plant an effective amount of the one or more plant growth-promoting microbial isolates comprises contacting seed of the plant with the one or more plant growth-promoting microbial isolates, adding the one or more plant growth-promoting microbial isolates to soil in which the plant is growing or will grow, and/or contacting a part of the plant with the one or more plant growth-promoting microbial isolates.

19. The method of claim 13, wherein the plant is a dicotyledon, a crop plant, or a legume.

* * * * *